US011964015B2

(12) United States Patent
Leuchs et al.

(10) Patent No.: US 11,964,015 B2
(45) Date of Patent: Apr. 23, 2024

(54) CANCER THERAPY WITH AN ONCOLYTIC VIRUS COMBINED WITH A CHECKPOINT INHIBITOR

(71) Applicants: DEUTSCHES KREBSFORSCHUNGSZENTRUM, Heidelberg (DE); RUPRECHT-KARLS-UNIVERSITAT HEIDELBERG, Heidelberg (DE)

(72) Inventors: Barbara Leuchs, Heidelberg (DE); Antonio Marchini, Heidelberg (DE); Jean Rommelaere, Heidelberg (DE); Assia Angelova, Heidelberg (DE); Dirk Jager, Mainz-Kostheim (DE); Wolfgang Wick, Heidelberg (DE); Michael Dahm, Munich (DE)

(73) Assignees: DEUTSCHES KREBSFORSCHUNGSZENTRUM, Heidelberg (DE); RUPRECHT-KARLS-UNIVERSITAT HEIDELBERG, Heidelberg (DE)

( * ) Notice: Subject to any disclaimer, the term of this patent is extended or adjusted under 35 U.S.C. 154(b) by 233 days.

(21) Appl. No.: 17/226,199

(22) Filed: Apr. 9, 2021

(65) Prior Publication Data
US 2021/0228714 A1 Jul. 29, 2021

Related U.S. Application Data

(60) Division of application No. 16/148,257, filed on Oct. 1, 2018, now Pat. No. 11,027,013, which is a continuation-in-part of application No. PCT/EP2017/056886, filed on Mar. 22, 2017.

(30) Foreign Application Priority Data

Apr. 1, 2016 (EP) .................................... 16163555
May 27, 2016 (EP) .................................... 16020193

(51) Int. Cl.
*A61K 35/768* (2015.01)
*A61K 39/395* (2006.01)
*A61K 45/06* (2006.01)
*A61P 35/00* (2006.01)
*C07K 16/28* (2006.01)
*A61K 39/00* (2006.01)

(52) U.S. Cl.
CPC ...... *A61K 39/39541* (2013.01); *A61K 35/768* (2013.01); *A61K 39/3955* (2013.01); *A61K 45/06* (2013.01); *A61P 35/00* (2018.01); *C07K 16/2818* (2013.01); *A61K 2039/505* (2013.01); *A61K 2039/54* (2013.01); *C07K 2317/21* (2013.01); *C07K 2317/24* (2013.01); *C12N 2750/14332* (2013.01)

(58) Field of Classification Search
CPC ............ A61K 39/39541; A61K 35/768; A61K 45/06; A61K 2039/54; A61P 35/00; C07K 16/2818
USPC ........................................................ 424/133.1
See application file for complete search history.

(56) References Cited

U.S. PATENT DOCUMENTS

| | | | |
|---|---|---|---|
| 7,179,456 B2 | 2/2007 | Rommelaere | |
| 8,217,149 B2 | 7/2012 | Irving et al. | |
| 8,414,883 B2 | 4/2013 | Rommelaere | |
| 9,333,225 B2 | 5/2016 | Kis | |
| 9,446,099 B2 | 9/2016 | Kipriljanova | |
| 9,592,260 B2 | 3/2017 | Marchini | |
| 9,700,588 B2 * | 7/2017 | Rommelaere | ........... A61P 35/00 |
| 9,861,669 B2 | 1/2018 | Rommelaere | |
| 10,058,591 B2 | 8/2018 | Raykov | |
| 10,624,935 B2 | 4/2020 | Leuchs | |

FOREIGN PATENT DOCUMENTS

| | | |
|---|---|---|
| EP | 2 397 542 A1 | 12/2011 |
| WO | 2009083232 A1 | 7/2009 |
| WO | 2009/101611 A1 | 8/2009 |
| WO | 2010139401 A1 | 12/2010 |
| WO | 2013/079174 A1 | 6/2013 |
| WO | 2015010782 A1 | 1/2015 |
| WO | 2015/138920 A1 | 9/2015 |
| WO | 2016009017 A1 | 1/2016 |

OTHER PUBLICATIONS

Karishma Rajani, et al., Combination Therapy With Reovirus and Anti-PD-1 Blockade Controls Tumor Growth Through Innate and Adaptive Immune Responses, The American Society of Gene & Cell Therapy (2016) vol. 24, No. 1, p. 166-174.
Norman Woller, et al., Oncolytic Viruses as Anticancer Vaccines, Frontiers in Oncology, Review Article, Jul. 21, 2014, vol. 4, Article 188, p. 1-13.
Justin C. Paglino, et al., LuIII Parvovirus Selectively and Efficiently Targets, Replicates in, and Kills Human Glioma Cells, Journal of Virology (Jul. 2012) vol. 86, No. 13, p. 7280-7291.
Suzanne L. Topalian, et al., Safety, Activity, and Immune Correlates of Anti-PD-1 Antibody in Cancer, The New England Journal of Medicine (Jun. 28, 2012) vol. 366, No. 26, p. 2443-2454.
Rauf Bhat, et al., NK-cell-dependent killing of colon carcinoma cells is mediated by natural cytotoxicity receptors (NORs) and stimulated by parvovirus infection of target cells, BMC Cancer (2013) 13:367.
Rauf Bhat, et al., Enhancement of NK cell antitumor responses using an oncolytic parvovirus, International Journal of Cancer (2011) 128:908-919.
Thorsten Fuereder, Immunotherapy for head and neck squamous cell carcinoma, Memo (2016) 9:66-69.

(Continued)

*Primary Examiner* — Yan Xiao
(74) *Attorney, Agent, or Firm* — Duane Morris LLP; Thomas J. Kowalski; Deborah L. Lu

(57) ABSTRACT

The present invention concerns a pharmaceutical composition where a checkpoint inhibitor is combined with an oncolytic virus and the use of said combination for the treatment of cancer.

6 Claims, 16 Drawing Sheets

Specification includes a Sequence Listing.

(56) References Cited

OTHER PUBLICATIONS

Karsten Geletneky, et al., Improved Killing of Human High-Grade Glioma Cells by Combining Ionizing Radiation with Oncolytic Parvovirus H-1 Infection, Journal of Biomedicine and Biotechnology, vol. 2010, Article ID 350748, 9 pages.
Karsten Geletneky, et al., Regression of advanced rat and human gliomas by local or systemic treatment with oncolytic parvovirus H-1 in rat models, Neuro-Oncology (2010) 12(8):804-814.
Karsten Geletneky, et al., Phase I/IIa study of intratumoral/intracerebral or intravenous/intracerebral administration of Parvovirus H-1 (ParvOryx) in patients with progressive primary or recurrent glioblastoma multiforme: ParvOryx01 protocol, BMC Cancer (2012) 12:99.
Bernd Heinrich, et al., Influence of the oncolytic parvovirus H-1, CTLA-4 antibody tremelimumab and cytostatic drugs on the human immune system in a human in vitro model of colorectal cancer cells, OncoTargets and Therapy (2013):6 1119-1127.
Markus Moehler, et al., Oncolytic virotherapy as emerging immunotherapeutic modality: potential of parvovirus H-1, Frontiers in Oncology. Tumor Immunity (May 2014) vol. 41, Article 92, 1-10.
Douglas B. Johnson, et al., Talimogene laherparepvec (T-VEC) for the treatment of advanced melanoma, Immunotherapy (Jul. 2015) 7(6): 611-619.
Neal Dharmadhikari, et al., Oncolytic Virus Immunotherapy for Melanoma, Curr. Treat. Options in Oncol. (2015) 16:10.
Karsten Geletneky, et al., Oncolytic H-1 Parvovirus Shows Safety and Signs of Immunogenic Activity in a First Phase I/IIa Glioblastoma Trial, Molecular Therapy (Dec. 2017) vol. 25 No. 12, p. 2620-2634.
Omid Hamid, MD, et al., Safety and Tumor Responses with Lambrolizumab (Anti-PD-1) in Melanoma, N Engl J Med. (Jul. 11, 2013) 369(2) p. 1-18.
Sonia Tusell Wennier, et al., Bugs and Drugs: Oncolytic Virotherapy in Combination with Chemotherapy, Curr Pharm Biotechnol. (Jul. 2012) 13(9): 1817-1833.

\* cited by examiner

Biopsy 1 (CD3)

Biopsy 1 (CD8)

Biopsy 1 (PD-1)

Biopsy 2 (CD3)

Biopsy 2 (CD8)

Biopsy 2 (PD-1)

Biopsy 3 (CD3)

Biopsy 3 (CD8)

Biopsy 3 (PD-1)

1st biopsy vs. 2nd biopsy

1st biopsy vs. 2nd biopsy

Baseline vs. 2nd biopsy

MRI of progressing recurrent GBM left temporal-parietal

CANCER THERAPY WITH AN ONCOLYTIC VIRUS COMBINED WITH A CHECKPOINT INHIBITOR

RELATED APPLICATIONS AND INCORPORATION BY REFERENCE

This application is a divisional of application Ser. No. 16/148,257 filed Oct. 1, 2018, now allowed, which is a continuation-in-part to international application Serial No. PCT/EP2017/056886 filed Mar. 22, 2017 and published as Publication No. WO2017/167626 on Oct. 5, 2017, claiming the benefit of priority from EP Patent Application Nos. EP16163555.2 filed Apr. 1, 2016 and EP 16020193.5 filed May 27, 2016. The content of each of the aforementioned Patent Applications is incorporated herein by reference in its entirety.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing which has been filed electronically in ASCII format and is hereby incorporated by reference in its entirety. Said ASCII copy, is named 00015Sequence_Listing.txt and is 2 bytes in size.

FIELD OF THE INVENTION

The present invention concerns a pharmaceutical composition where a checkpoint inhibitor is combined with an oncolytic virus and the use of said combination for the treatment of cancer.

BACKGROUND OF THE INVENTION

Cancer is the second leading cause of death worldwide. It has been estimated that half of men and one third of women will be diagnosed with some form of cancer during their lifespan. Moreover, because cancer is predominantly a disease of aging, the number of cancer deaths worldwide is predicted to increase about 45% from 2007 to 2030 (from 7.9 million to 11.5 million deaths) due to the increase proportion of elderly people (WHO estimates, 2008). Cancer is also the most costly disease. The latest estimates from the National Cancer Institute showed that the overall economic cost of cancer in the U.S. in 2007 was $226.8 billion and unless more successful preventive interventions, early detection and more efficient treatments will be developed, this already huge economic burden is expected to further grow during the next two decades. Despite significant progresses in the prevention, detection, diagnosis and treatment of many forms of cancer, which is testified by an increase of the percentage of 5-years cancer survivals in U.S. and in Europe over the last thirty years, some tumor types, such as pancreatic, liver, lung, brain remain orphan of effective treatments calling for the development of new therapeutic options. Oncolytic viruses, which exploit cancer-specific vulnerabilities to kill cancer cells while sparing normal cells are fast emerging as promising tools for fighting cancer (Breitbach et al, 2011; Russell et al. 2012). No less than twelve different oncolytic viruses are currently undergoing phase I-III clinical trials against various malignancies (Russell et al, 2012) used alone or in combination with other anticancer agents. Among them, the oncolytic rat parvovirus H-1PV is currently evaluated for safety and first signs of efficacy in a phase I/IIa clinical trial in patients having recurrent glioblastoma multiforme (GBM) (Geletneky et al, 2012).

H-1PV is a small (~25 nm in diameter), non-enveloped icosahedral particle containing a 5.1 kb long single-stranded DNA genome (Cotmore & Tattersall, 2007). The genomic organization of H-1PV consists of two transcriptional units under the control of two promoters, the P4 early promoter and P38 late promoter. P4 regulates the expression of the gene encoding for the non-structural (NS) proteins (NS1 and NS2) and the P38 the one encoding for the capsid (VP) proteins (VP1, VP2, VP3) (Cotmore & Tattersall, 2007). The virus multiplies preferentially in fast dividing cancer cells. This onco-selectivity is not based on a better uptake of the virus by cancerous cells, but rather is due to the fact that cancer cells overexpress factors such as cyclin A, E2F, or CREB/ATF required for virus DNA replication. Furthermore, cancer cells are often defective in their ability to mount an efficient antiviral immune response favouring viral multiplication (Nuesch et al, 2012). The virus is known to activate multiple cell death pathways. Depending on cell type and growing conditions, H-1PV may induce apoptosis (Hristov et al, 2010; Ohshima et al, 1998; Rayet et al, 1998; Ueno et al, 2001), necrosis (Ran et al, 1999), or cathepsin B-dependent cell death (Di Piazza et al, 2007). The virus was able to induce oncolysis even in cancer cells resistant to TRAIL (Tumor Necrosis Factor Related Apoptosis Inducing Ligand), cisplatin and even when Bcl-2 was overexpressed (di Piazza et al., 2007). The latter results suggest that Bcl-2 is not a negative modulator of parvovirus cytotoxicity. Cancer therapy using a parvovirus and its combination with chemotherapy or an HDAC inhibitor has been recently described (WO 2009/083232 A1; WO 2011/113600 A1).

The major non-structural protein NS1 is the master regulator of virus DNA replication, viral gene expression and cytotoxicity. The sole expression of NS1, similarly to the entire virus, is sufficient to induce cell cycle arrest, apoptosis and cell lysis via accumulation of reactive oxygen species and DNA damage (Hristov et al, 2010). As results of its oncolytic activities, the virus has been shown to possess oncosuppressive properties demonstrated in a number of animal models which lay the basis for the launch of the clinical trial against GBM (Geletneky et al, 2012).

During the last few years, in addition to therapy concepts based on oncolytic viruses, the field of immuno-oncology has become a valuable approach in the fight against cancer. One of the most recent promising approaches to activate therapeutic antitumor immunity is the blockade of immune checkpoints. Immune checkpoints refer to a plethora of inhibitory pathways hardwired into the immune system that are crucial for maintaining self-tolerance and modulating the duration and amplitude of physiological immune responses in peripheral tissues in order to minimize collateral tissue damage. It is now clear that tumors co-opt certain immune-checkpoint pathways as a major mechanism of immune resistance, particularly against T cells that are specific for tumor antigens. Because many of the immune checkpoints are initiated by ligand-receptor interactions, they can be readily blocked by antibodies or modulated by recombinant forms of ligands or receptors.

The huge number of genetic and epigenetic changes that are inherent to most cancer cells provide plenty of tumor-associated antigens that the host immune system can recognize, thereby requiring tumors to develop specific immune resistance mechanisms. An important immune resistance mechanism involves immune-inhibitory pathways, termed immune checkpoints, which normally mediate immune tolerance and mitigate collateral tissue damage. A particularly important immune-checkpoint receptor is cytotoxic T-lymphocyte-associated antigen 4 (CTLA4), which downmodulates the amplitude of T cell activation. In normal physiology T-cells are activated by two signals: the T-cell receptor binding to an antigen-MHC complex and T-cell receptor CD28 binding to CD80 and CD 86 on the surface of the antigen presenting cells. CTLA4 binds to CD80 or CD86 which prevents the binding of CD28 to these surface proteins and therefore negatively regulates the activation of T-cells. Active cytotoxic T-cells are required for the immune system to attack cancer cells whereas regulatory T-cells inhibit other T-cells which may benefit the tumor. Antibody blockade of CTLA4 in cancer induced antitumor immunity in view of a shift in the ratio of regulatory T-cells to cytotoxic T-cells. Thus, increasing the amount of cytotoxic T-cells and decreasing the regulatory T-cells increases the anti-tumor response. Clinical studies using antagonistic CTLA4 antibodies demonstrated activity in melanoma. Despite a high frequency of immune-related toxicity, this therapy enhanced survival in two randomized Phase III trials. Anti-CTLA4 therapy was the first agent to demonstrate a survival benefit in patients with advanced melanoma and was approved by the US Food and Drug Administration (FDA) in 2010 (Pardoll, D., Nature Reviews Cancer, Vol. 12, pp. 252-264, (2012)). The approved anti-CTLA4 antibody is known under the name "ipilimumab" and marketed under the brandname "Yervoy®" by Bristol Myers Squibb (BMS).

Some immune-checkpoint receptors, such as programmed cell death protein 1 (PD1), limit T cell effector functions within tissues. By upregulating ligands for PD1, tumor cells block antitumor immune responses in the tumor microenvironment. Clinical findings with blockers of additional immune-checkpoint proteins, such as programmed cell death protein 1 (PD1), indicate broad and diverse opportunities to enhance antitumor immunity with the potential to produce durable clinical responses. Clinical trials suggest that blockade of the PD1 pathway induces sustained tumor regression in various tumor types. Responses to PD1 blockade may correlate with the expression of PD1 ligands by tumor cells.

On Sep. 4, 2015 the FDA approved the humanized monoclonal antibody pembrolizumab (also known as MK-3575 or Keytruda® marketed by Merck Sharp Dohme; MSD) that is directed against the target PD-1 under the FDA Fast Track Development Program. It is approved for use following treatment with ipilimumab (which is directed against CTLA4), or after treatment with ipilimumab and a BRAF inhibitor in advanced melanoma patients who carry a BRAF mutation.

On Sep. 30, 2015 the FDA granted accelerated approval to another anti-PD1 antibody (nivolumab; Opdivo® Injection marketed by Bristol Myers Squibb; BMS) in combination with anti-CTLA4 antibody ipilimumab for the treatment of patients with BRAF V 600 wild-type, unresectable or metastatic melanoma.

Multiple additional immune-checkpoint receptors and ligands, some of which are selectively upregulated in various types of tumor cells, are prime targets for blockade, particularly in combination with approaches that enhance the activation of antitumor immune responses, such as vaccines.

Anti-PD-L1 antibodies and methods of making the same are known in the art. Such antibodies to PD-L1 may be polyclonal or monoclonal, and/or recombinant, and/or humanized. Examples of antibodies to PD-L1 are disclosed in U.S. Pat. No. 8,217,149, U.S. application Ser. No. 13/511,538, U.S. application Ser. No. 13/478,511.

Exemplary agents that target immune-checkpoint pathways are shown in the following Table 1 (modified from Pardoll, D., Nature Reviews Cancer, Vol. 12, pp. 252-264, (2012):

| Target | Biological Function | Antibody or Ig fusion protein |
| --- | --- | --- |
| Surface protein CTLA4 | Inhibitory receptor | Ipilimumab (brandname: Yervoy ® marketed by BMS) Tremelimumab (also known as ticilimumab or CP-675,206) |
| Programmed cell death 1 (PD-)1 receptor | Inhibitory receptor | MDX-1106 (also known as BMS-936558 or nivolumab, brandname: Opdivo ® marketed by BMS) MK 3475 (also known as pembrolizumab or lambrolizumab, brandname: Keytruda ® marketed by MSD) CT-011 AMP-224 |
| PDL 1 | Ligand for PD1 | MDX-1105 |
| LAG3 | Inhibitory receptor | IMP321 |
| B7-H3 | Inhibitory ligand | MGA271 |

Although for some tumor types (e.g. melanoma, lung) the treatment with checkpoint inhibitors shows promising results, it has been recognized that patients with some other tumors (e.g. colon, pancreas) do not benefit from such a treatment.

Citation or identification of any document in this application is not an admission that such document is available as prior art to the present invention.

SUMMARY OF THE INVENTION

Therefore, it is the object of the present invention to provide means for an improved cancer therapy and to make a larger range of tumors susceptible to checkpoint inhibitor treatment.

According to the invention this is achieved by the subject matters defined in the claims.

In the study resulting to the present invention it was asked whether a checkpoint inhibitor, e.g. an anti-PD1 antibody like pembrolizumab, synergizes with an oncolytic virus, e.g.

a parvovirus like H-1PV or a related rodent parvovirus, in killing cancer cells. It was shown that the administration of pembrolizumab potentiates the oncolytic activity of the virus in a synergistic manner in several patients.

The present invention provides a pharmaceutical composition containing (a) an oncolytic virus in combination with (b) a checkpoint inhibitor. The present invention also provides the use of said pharmaceutical combination for treating cancer.

Preferably, in said pharmaceutical composition the oncolytic virus and the checkpoint inhibitor are present in an effective dose and combined with a pharmaceutically acceptable carrier.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 10: Increased/Upregulated Proteins in first biopsy: CTACK-CCL27, IL-16, SDF-1 alpha, IP-10, MIP-1b.

FIG. 11: Decreased/Downregulated Proteins in first biopsy:
G-CSF, IL-5, IL-7, IL-13, IL-12p40, FGP basic, MIF, SCGF-β, IL-1 alpha.

FIG. 12: Increased/Upregulated Proteins, first biopsy vs. second biopsy.

FIG. 13: Decreased/Downregulated Proteins, first biopsy vs. second biopsy.

FIG. 14: Increased/Upregulated Proteins in second biopsy.

FIG. 15: Decreased/Downregulated Proteins in second biopsy.

DETAILED DESCRIPTION OF THE INVENTION

Figure 1:
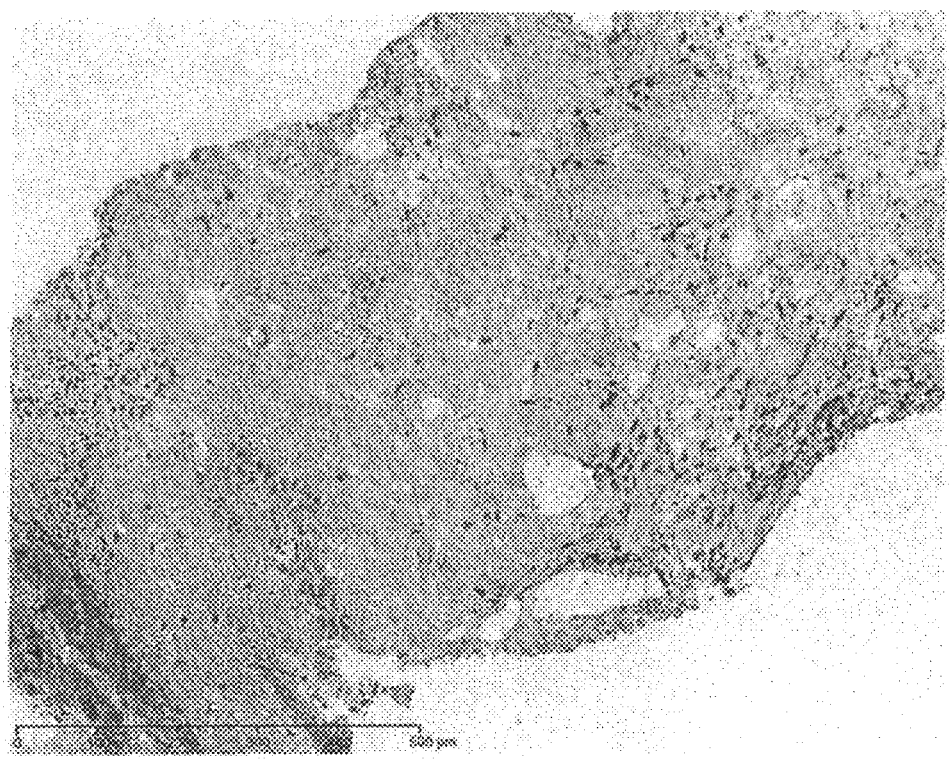
FIG. 1: Immunofluoresence of Biopsy 1 of liver metastasis (CD3) shows vital tumor areas, clear infiltrate of CD3 positive cells. Infiltrates are heterogenous.
Figure 2:
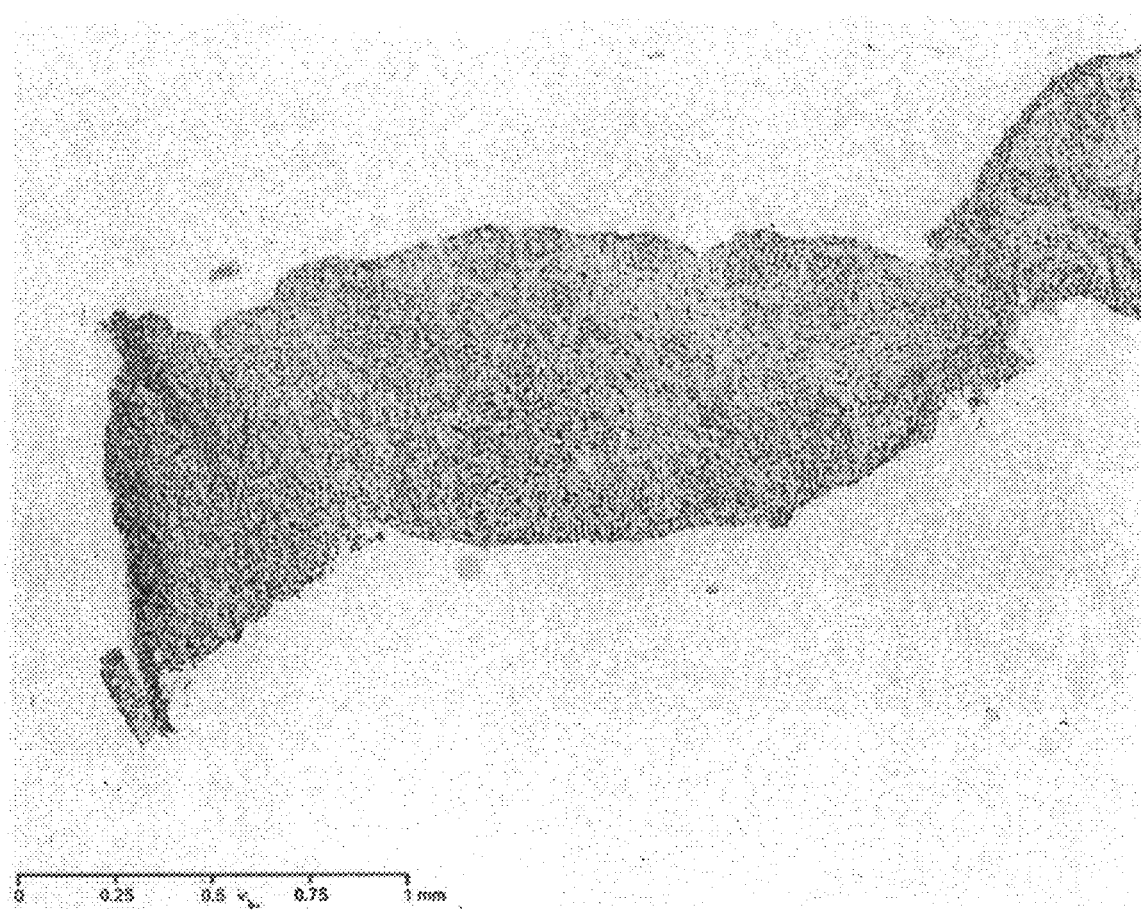
FIG. 2: Immunofluorescence of Biopsy 1 of liver metastasis (CD8) shows clear infiltrate of effector T cells, again, heterogenous. Interestingly, there is close vicinity of CD8+ T cells with tumor epithelium which is rare to be observed.
Figure 3:
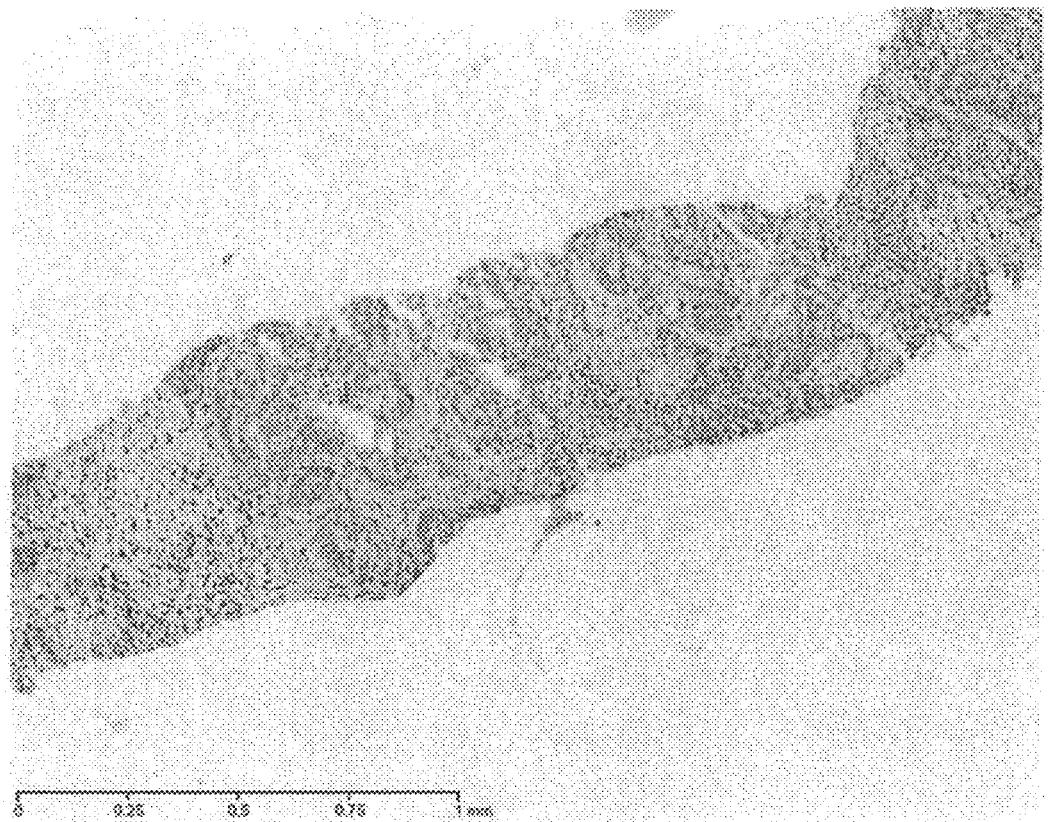
FIG. 3: Immunofluorescence of Biopsy 1 of liver metastasis (PD-1) shows that predominantly the stromal compartment is T cell rich. Most of them are PD1 positive.
Figure 4:
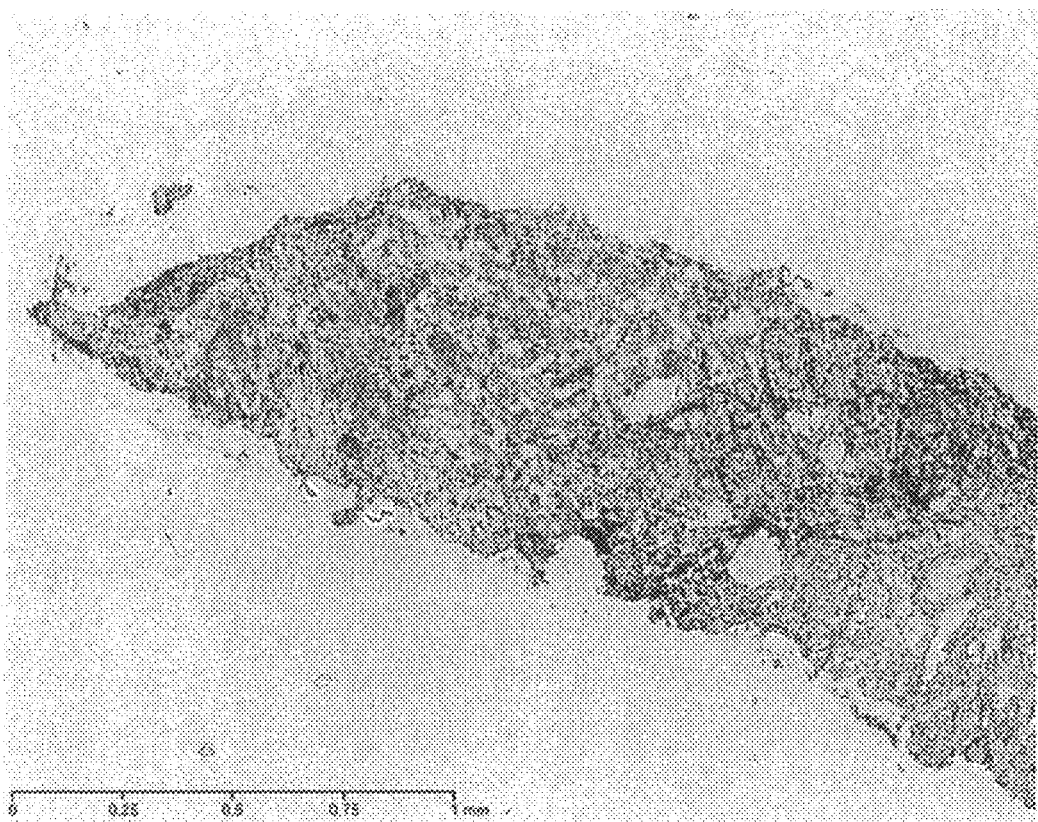
FIG. 4: Immunofluorescence of Biopsy 2 of liver metastasis (CD3) shows that after first infusion of H-1 PV+PD-1 antibody a significant increase in T cell density was observed (about +30-50%). Again heterogenous pattern.
Figure 4:
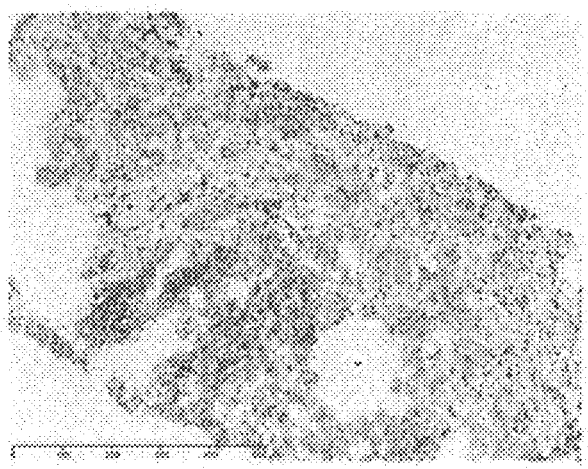
Figure 5:
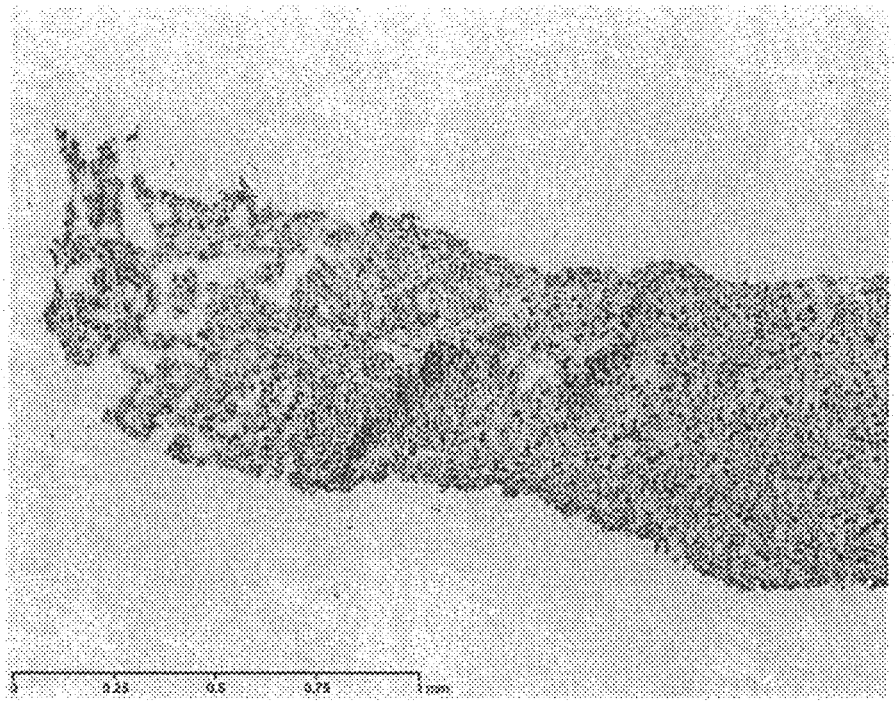
FIG. 5: Immunofluorescence of Biopsy 2 of liver metastasis (CD8) shows a significant increase in CD8+ T cell density. Very heterogenous. Close contact of CD8+ T cells with tumor cells.
Figure 5:
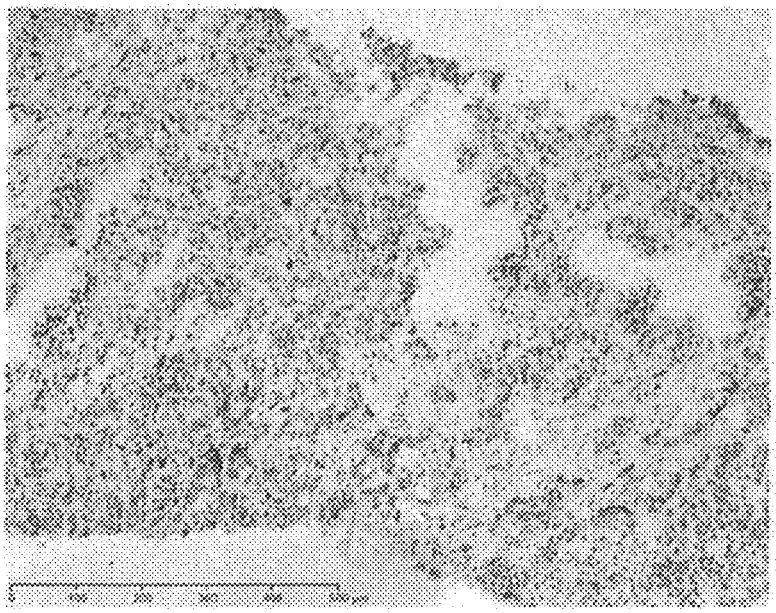
Figure 6:
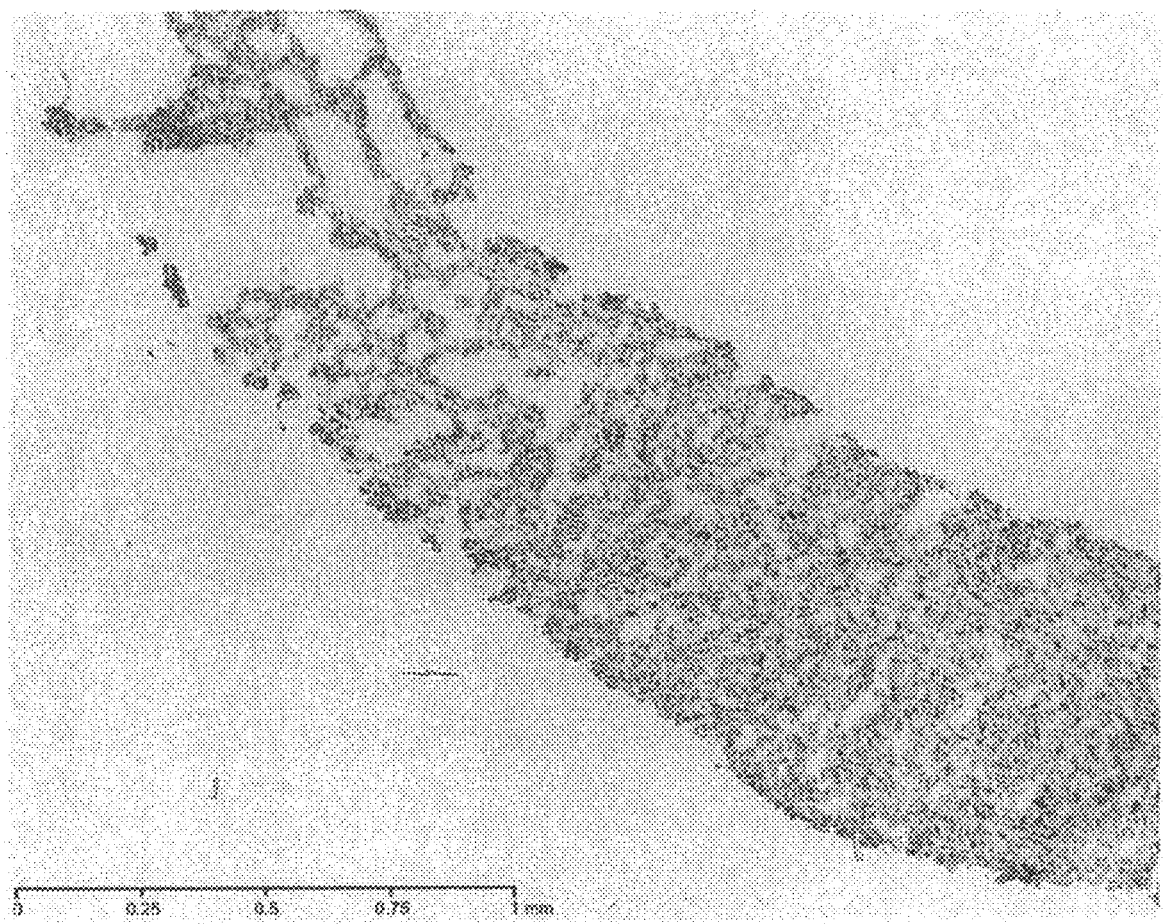
FIG. 6: Immunofluorescence of Biopsy 2 of liver metastasis (PD-1) shows that most T cells are PD-1 positive.
Figure 7:
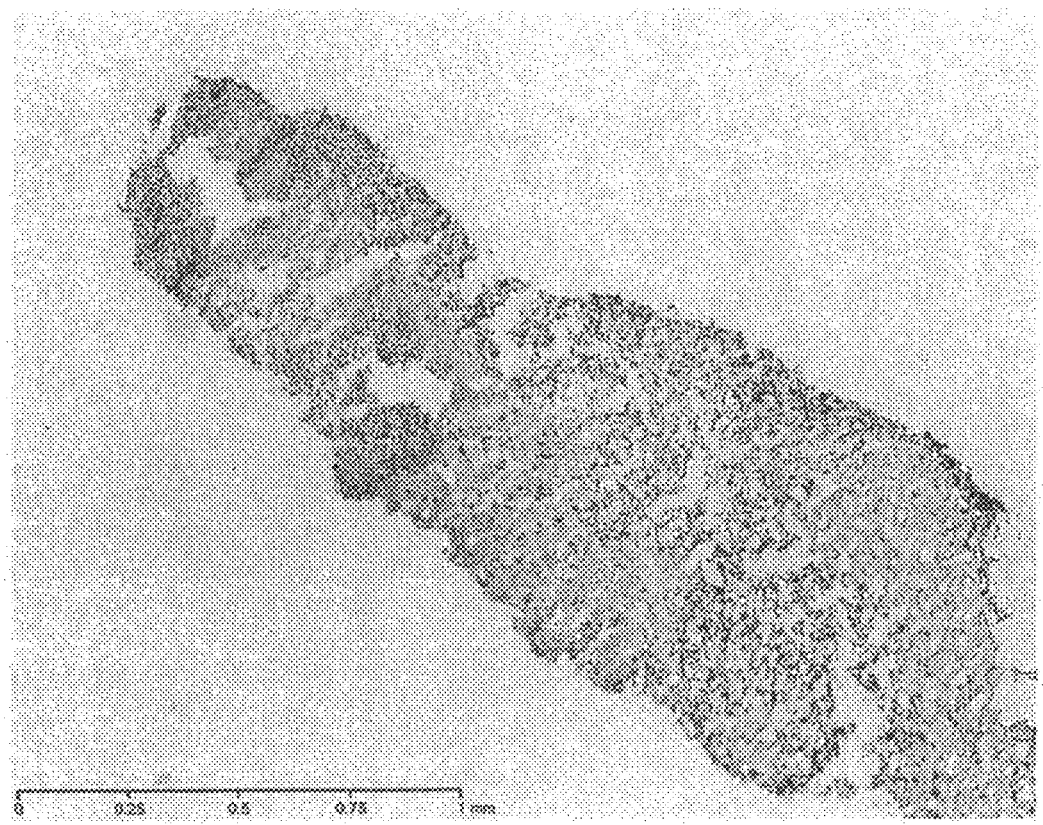
FIG. 7: Immunofluorescence of Biopsy 3 of liver metastasis (CD3) shows that after second infusion with H-1 PV+PD-1 antibody there is still increase in T cell density. Again very hetergenous.
Figure 8:
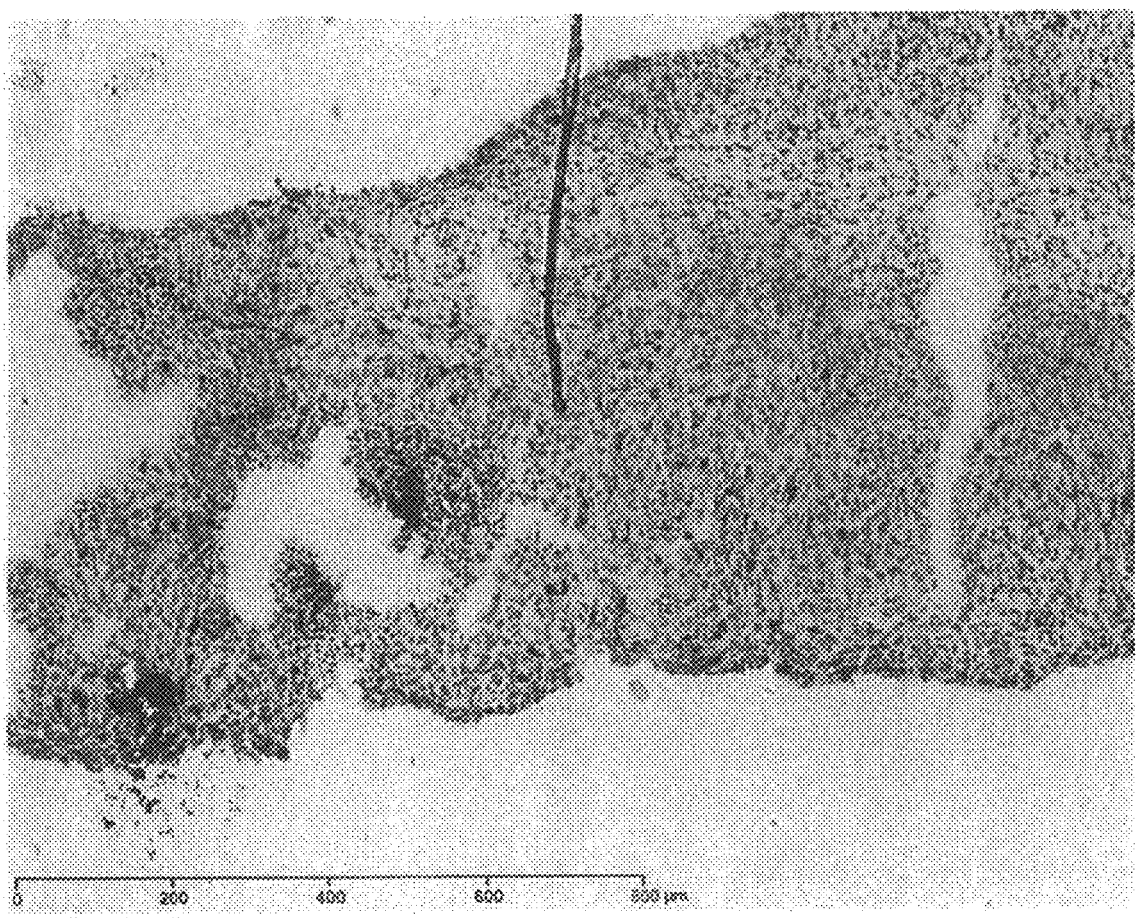
FIG. 8: Immunofluorescence of Biopsy 3 of liver metastasis (CD8) shows dense T cell infiltrates, similar to biopsy 2.
Figure 9:
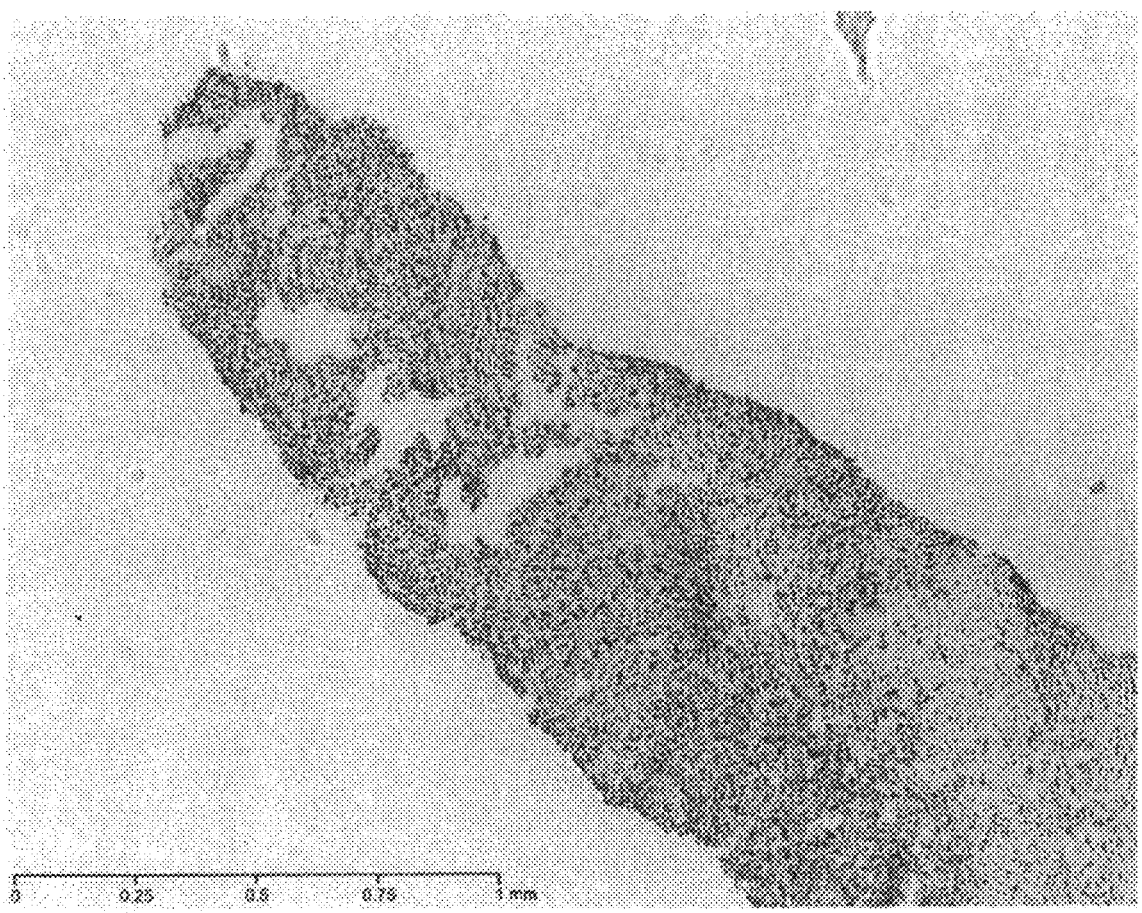
FIG. 9: Immunofluorescence of Biopsy 3 of liver metastasis (PD-1) shows that still most T cells are PD-1 positive.
Figure 10:
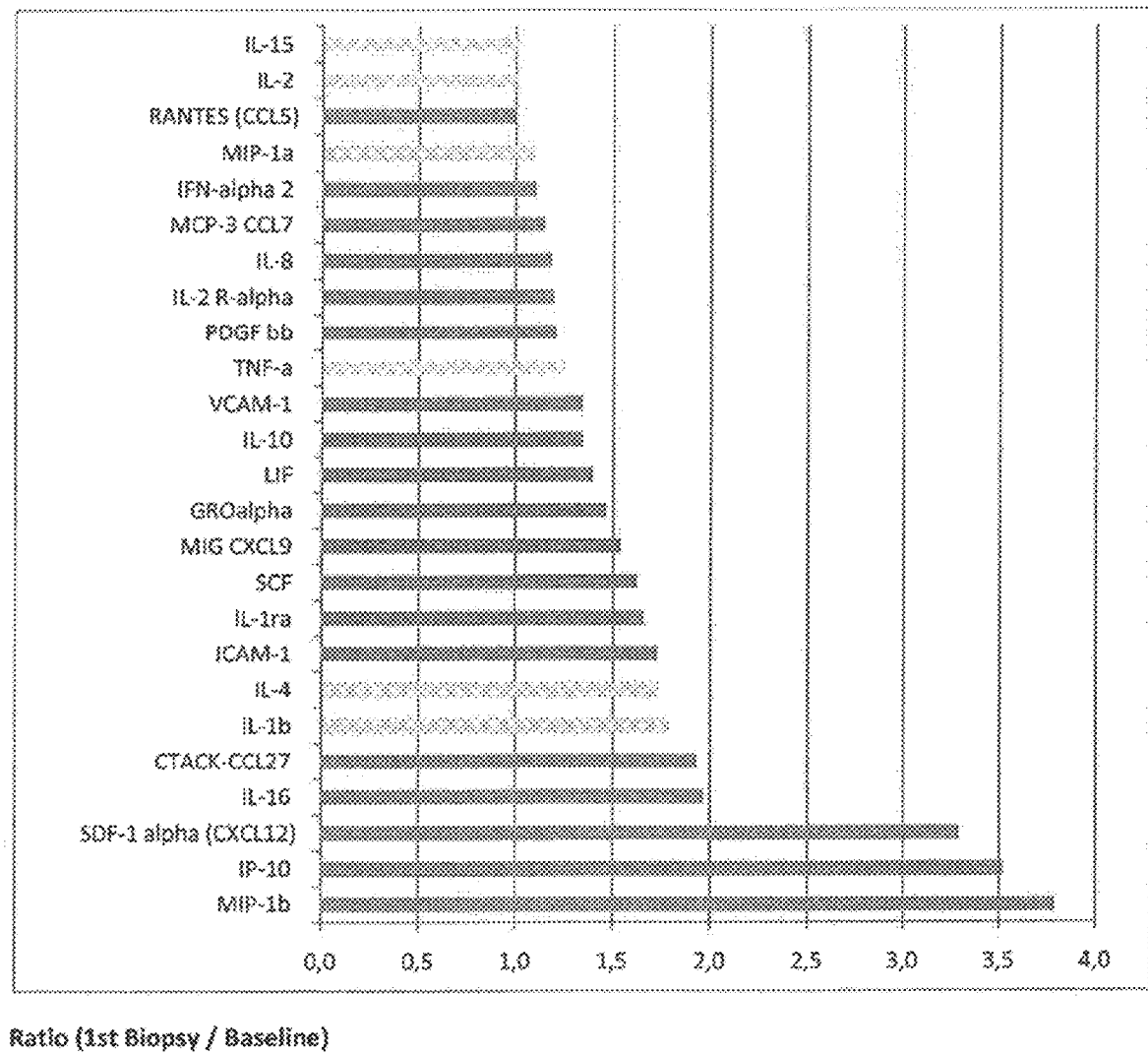
FIG. 10-15: Cytokine profiles
Data from Multiplex-Cytokine quantification
Reference for protein quantification
Equal protein amounts for each biopsy
Ratios are shown (dotted columns have too low proteins amounts to be robust).
Figure 11:
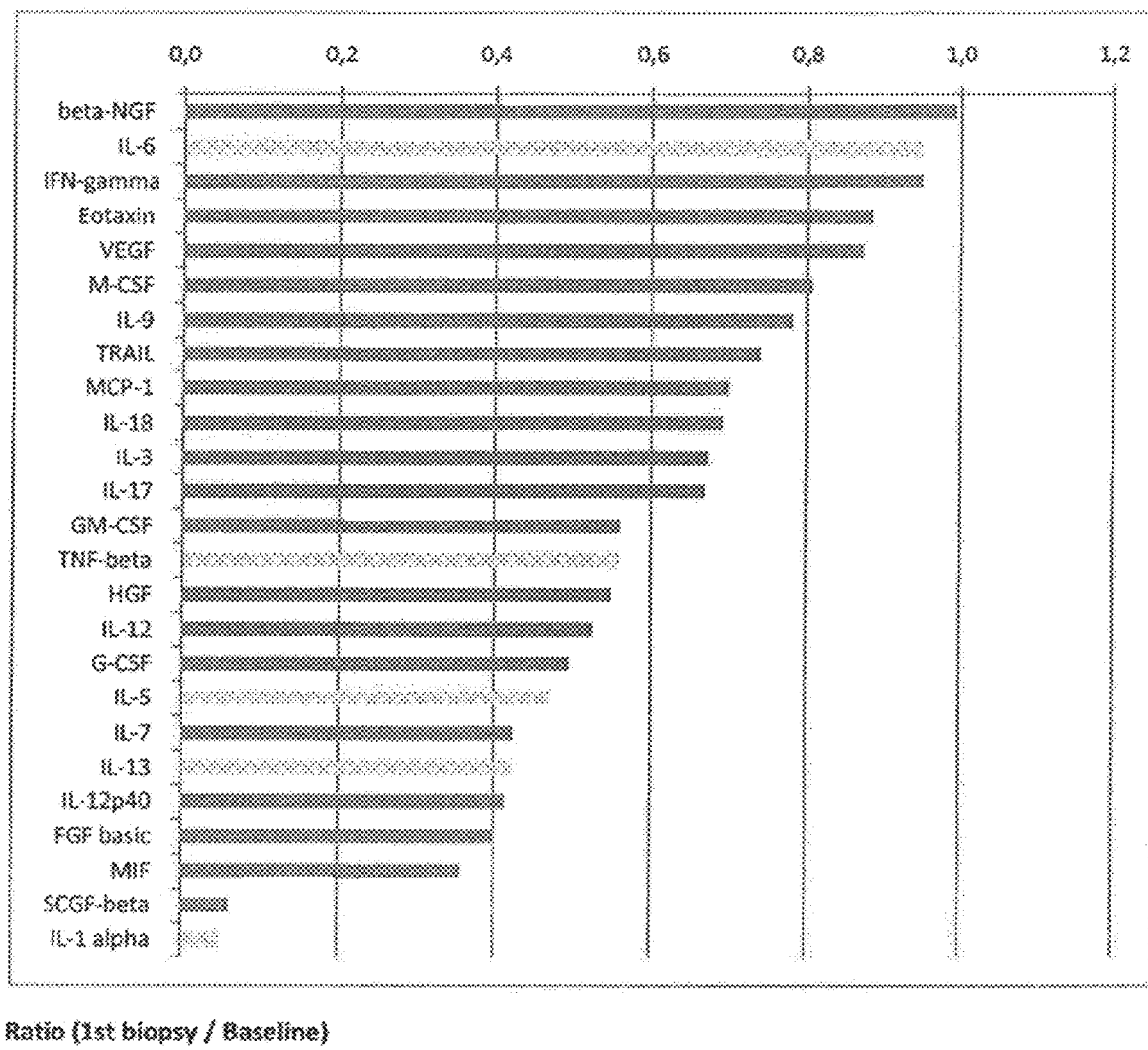
Figure 12:
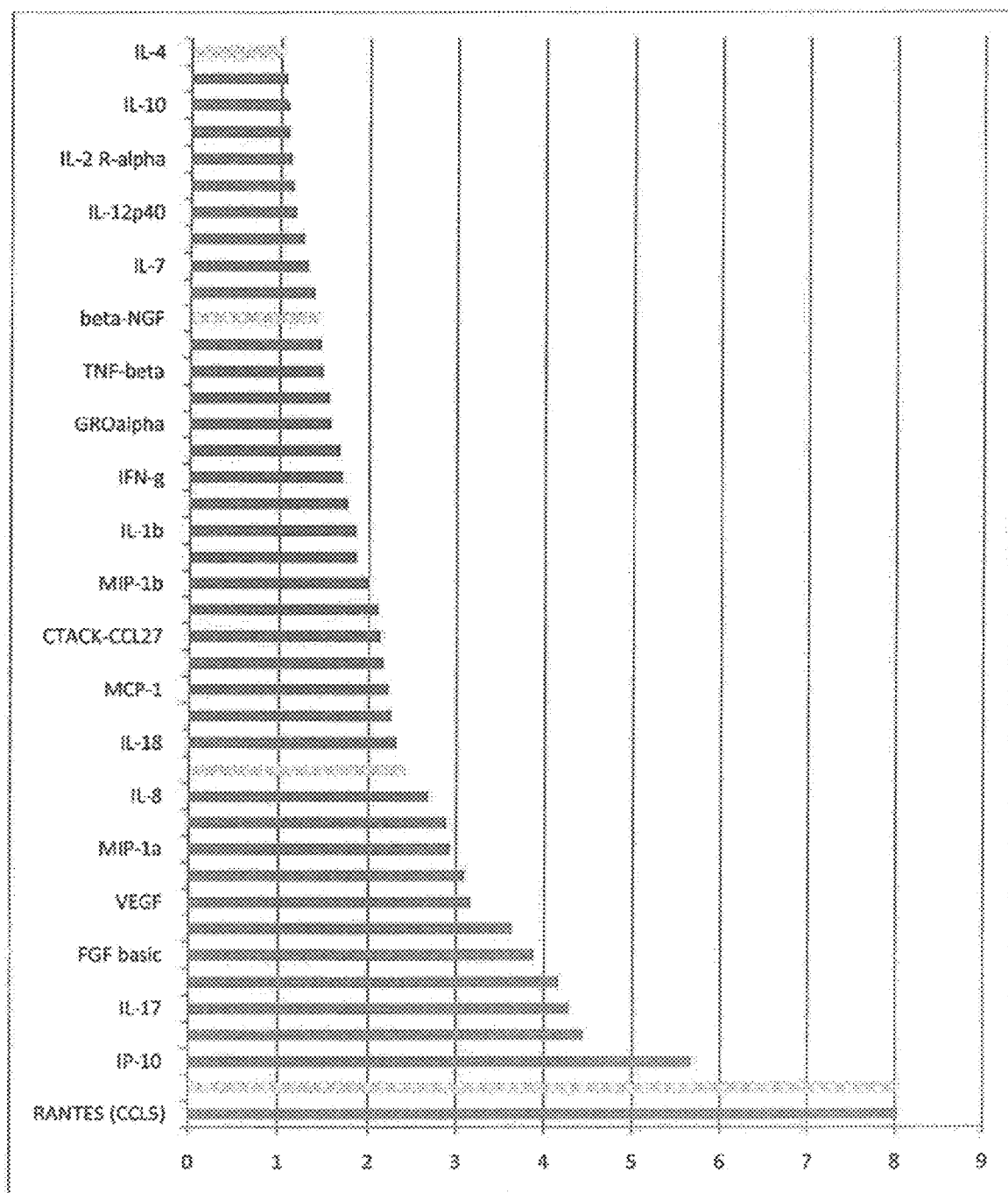
Figure 13:
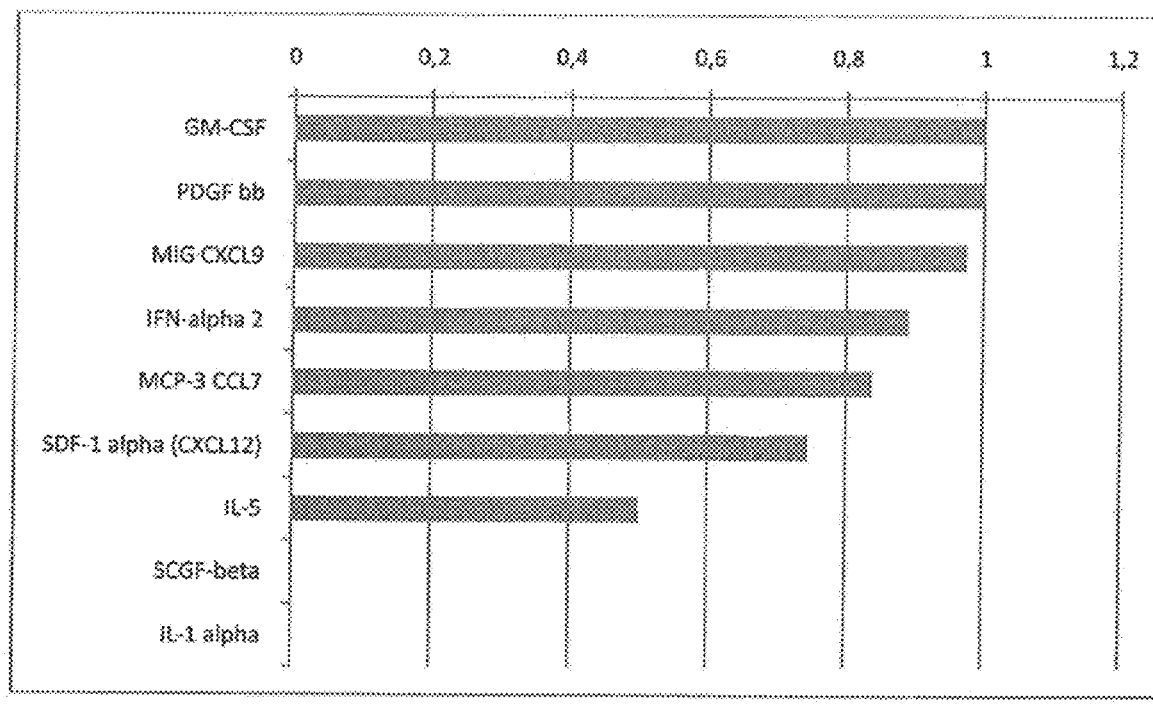
Figure 14:
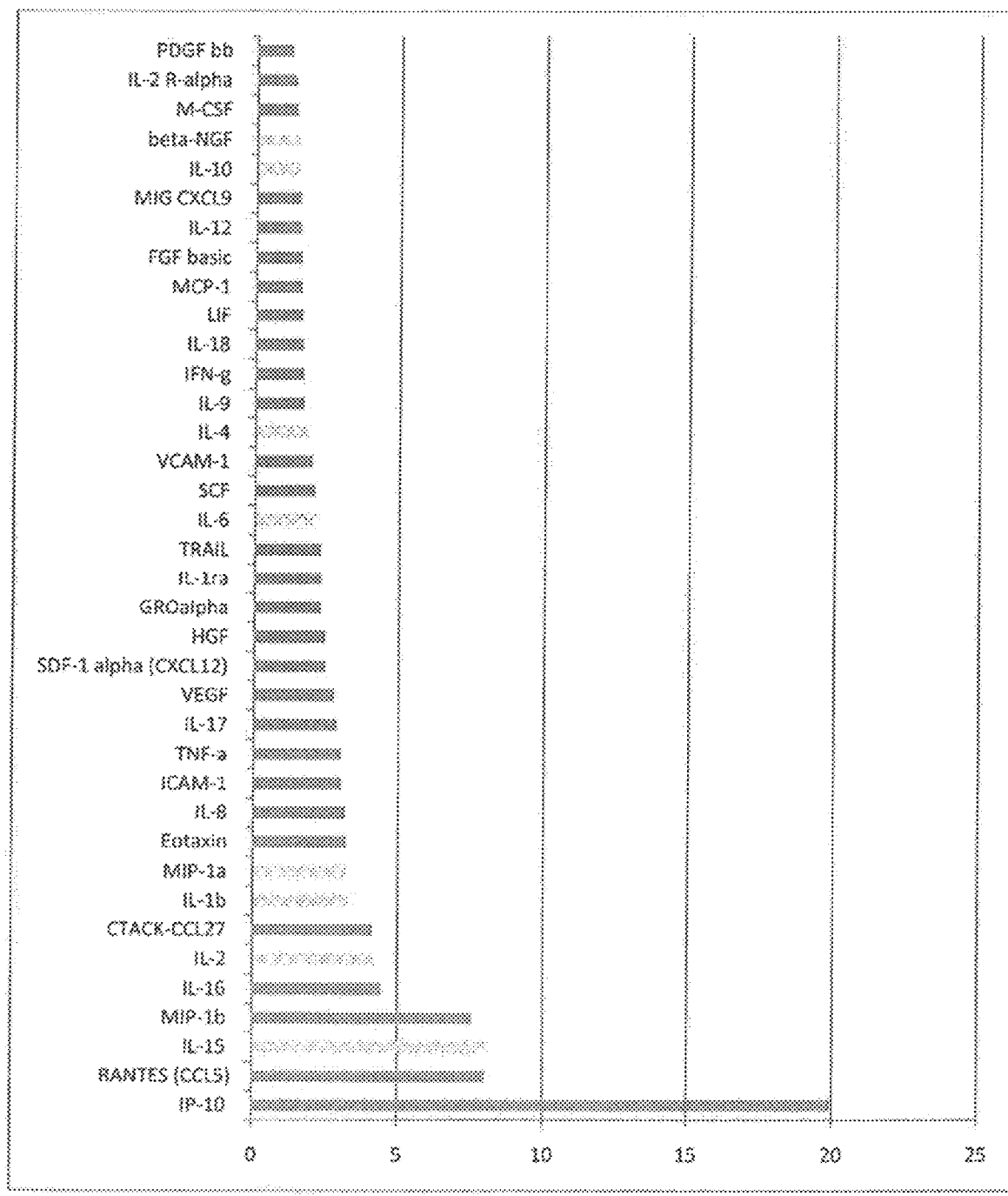
Figure 15:
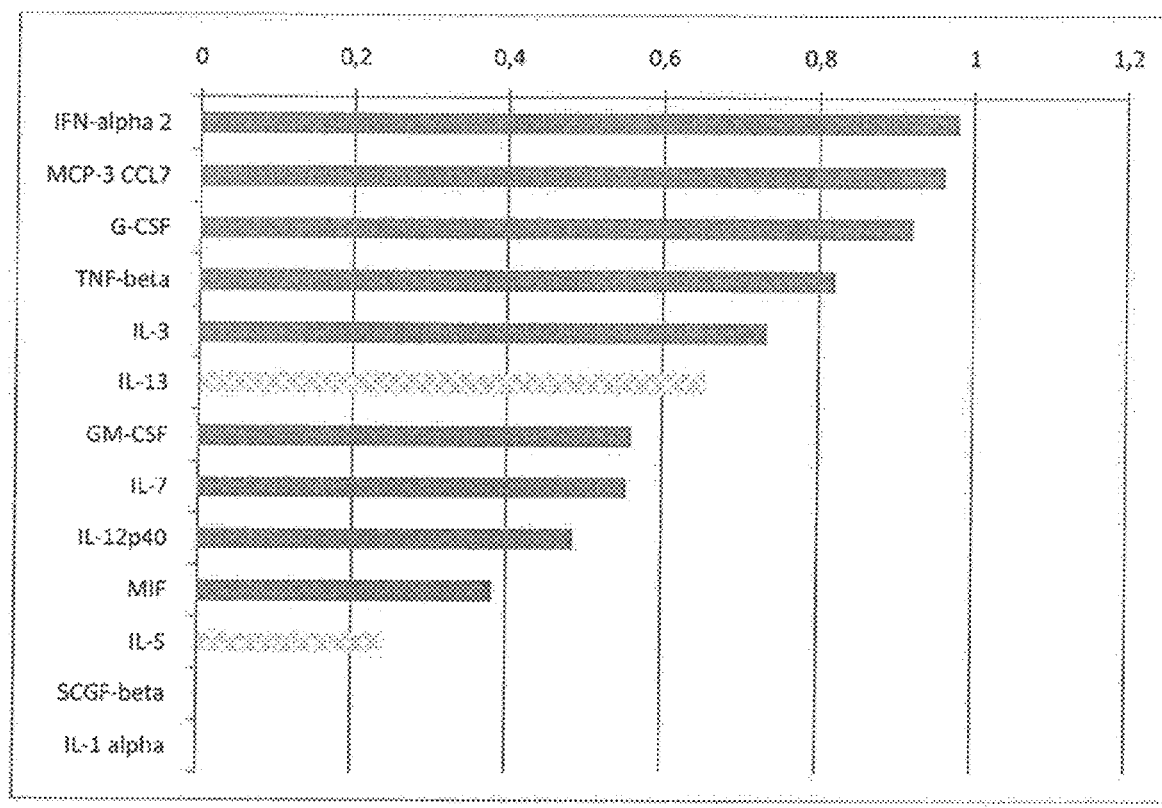

As used herein the term "agent" is understood to mean a substance that produces a desired effect in a tissue, system, animal, mammal, human, or other subject.

Accordingly, the term "anti-neoplastic agent" is understood to mean a substance producing an anti-neoplastic effect in a tissue, system, animal, mammal, human, or other subject. It is also to be understood that an "agent" may be a single compound or a combination or composition of two or more compounds.

By the term "treating" and derivates thereof as used herein, is meant therapeutic therapy. In reference to a particular condition, treating means: (1) to ameliorate the condition or one or more of the biological manifestations of the conditions, (2) to interfere with (a) one or more points in the biological cascade that leads to or is responsible for the condition or (b) one or more of the biological manifestations of the condition (3) to alleviate one or more of the symptoms, effects or side effects associated with the condition, or (4) to slow the progression of the condition or one or more of the biological manifestations of the condition.

As used herein, "prevention" is understood to refer to the prophylactic administration of a drug to substantially diminish the likelihood or severity of a condition or biological manifestation thereof, or to delay the onset of such condition or biological manifestation thereof. The skilled artisan will appreciate that "preventions" is not an absolute term. Prophylactic therapy is appropriate, for example, when a subject is considered at high risk for developing cancer, such as when a subject has a strong family history of cancer or when a subject has been exposed to a carcinogen.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder or side effect. The term also includes within its scope amounts effective to enhance normal physiological function. An "effective dose" useful for treating and/or preventing these diseases or disorders may be determined using methods known to one skilled in the art.

The administration of a therapeutically effective amount of the combinations of the invention are advantageous over the individual component compounds in that the combinations provide one or more of the following improved properties when compared to the individual administration of a therapeutically effective amount of a component compound: i) a greater anticancer effect than the most active single agent, ii) synergistic or highly synergistic anticancer activity, iii) a dosing protocol that provides enhanced anticancer activity with reduced side effect profile, iv) a reduction in the toxic effect, profile, v) an increase in the therapeutics window, or vi) an increase in the bioavailability of one or both of the component compounds.

"Pharmaceutically acceptable" is meant to encompass any carrier, which does not interfere with the effectiveness of the biological activity of the active ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at an effective dose. Additional pharmaceutically compatible carriers can include gels, bioadsorbable matrix materials, implantation elements containing the therapeutic agent, or any other suitable vehicle, delivery or dispensing means or material(s).

As used herein the term "cancer" refers to an abnormal growth of cells or tissue and is understood to include malignant neoplastic growths. The term "neoplastic" means of or related to a neoplasm. In some embodiments the cancer is a solid tumor, i.e. brain cancer (particularly gliomas: ependymomas, astrocytomas [e.g. glioblastoma multiforme], oligodendrogliomas, brainstem glioma, oligoastrocytomas); colon cancer (in particular non-MSI CRC), bladder cancer, liver cancer, breast cancer (particularly double or triple negative breast cancer), kidney cancer, head/neck squamous cell carcinoma, lung cancer (particularly lung squamous cell carcinoma, non-small-cell lung cancer (NSCLS), small-cell lung cancer (SCLC)), malignant melanoma, ovarian cancer, pancreatic cancer, prostate cancer, renal cell cancer or stomach cancer. The term "cancer" also encompasses metastasis' of the mentioned tumors in various organs. In a preferred embodiment these tumors are resistant to parvovirus toxicity. In a further preferred embodiment these tumor to be treated are recurrent tumors. A particular advantage of the pharmaceutical composition of the present invention is that even cancer initiating stem cells can be successfully treated. This has a positive effect as regards the avoidance of the recurrence of the tumors and metastasis formation.

In other embodiments the cancer is a heme malignancy, i.e. acute lymphoblastic leukemia (ALL), acute myeloid leukemia (AML), chronic lymphocytic leukemia (CLL), chronic myeloid leukemia (CML), diffuse large B-cell lymphoma (DLBCL), EBV-positive DLBCL, primary mediasinal large B-cell lymphoma, T-cell(histiocyte)-rich large B-cell lymphoma, follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL).

"Checkpoint inhibitor" means any agent that cause a blockade of immune system inhibitory checkpoints. Blockade of inhibitory immune checkpoints activates immune system function. Suitable targets and agents are mentioned in Table 1 to which reference is made. In a preferred embodiment the ligand-receptor interaction as a target for cancer treatment is the interaction between the transmembrane programmed cell death 1 protein (PDCD1, PD-1, also known as CD279) and its ligand, PD-1 ligand (PD-L1, CD274). In normal physiology PD-L1 on the cell surface binds to PD-1 on an immune cell surface, which inhibits immune cell activity.

Upregulation of PD-L1 on the cancer cell surface may allow them to evade the patient's immune system by inhibiting T cells that might otherwise attack the tumor cell. Antibodies that bind to either PD-1 or PD-L1 and therefore block the interaction allow the T-cells to attack the tumor. Thus, in a preferred embodiment, PD-1 antagonists are used as checkpoint inhibitor.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCDIL2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus N.: NP_054862 and NP_079515, respectively.

PD-1 antagonists useful in the any of the treatment method, medicaments and uses of the present invention include monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the treatment method, medicaments and uses of the present invention, are described in U.S. Pat. Nos. 7,521,051, 8,008,449, and 8,354,509. Specific anti-human PD-1 mAbs useful as the PD-1 antagonist in the treatment method, medicaments and uses of the present invention include: MK-3475 (pembrolizumab), a humanized IgG4 mAb with the structure described in WHO Drug Information, Vol. 27, No. 2, pages 161-162 (2013); nivolumab (BMS-936558), a human IgG4 mAb with the structure described in WHO Drug Information, Vol. 27, No. 1, pages 68-69 (2013); the humanized antibodies h409A11, h409A16 and h409A17, which are described in WO2008/156712 A1.

It will be realized by those skilled in the art that any type of virus, which is potentially cytotoxic to tumor cells, may be employed in the combination of the present invention. Replication competent toxic viruses used in the invention may affect kill tumor by lysis, i.e. be oncolytic, or may kill tumor cells via a different mechanism. Particular examples of viruses for use in the practice of the invention include adenovirus, retrovirus, vesicular stomatitis virus, Newcastle Disease virus, polyoma virus, vaccinia virus, herpes simplex virus and parvovirus. Preferably the oncolytic virus is a parvovirus, more preferably parvovirus H-1 or a related rodent parvovirus selected from LuIII, Mouse minute virus (MMV), Mouse parvovirus (MPV), Rat minute virus (RMV), Rat parvovirus (RPV), or Rat virus (RV).

The term "oncolytic virus" and particularly "parvovirus" or "parvovirus H-1" as used herein may comprise wild-type or modified replication-competent derivatives thereof, as well as related viruses or vectors based on such viruses or derivatives. Suitable oncolytic viruses, derivatives, etc. as well as cells which can be used for actively producing said viruses and which are useful for therapy, are readily determinable within the skill of the art based on the disclosure herein, without undue empirical effort.

Administration of the compounds may be effected by different ways, e.g. by intravenous, intraperitoneal, subcutaneous, intramuscular, topical, intratumoral or intradermal administration. The route of administration, of course, depends on the kind of therapy and the kind of compounds contained in the pharmaceutical composition. The dosage regimen of the virus and checkpoint inhibitor is readily determinable within the skill of the art, by the attending physician based on patient data, observations and other clinical factors, including for example the patient's size, body surface area, age, sex, the particular virus, the particular inhibitor etc. to be administered, the time and route of administration, the tumor type and characteristics, general health of the patient, and other drug therapies to which the patient is being subjected. As regards the checkpoint inhibitors reference is made to the package insert and patient information sheet which are incorporated by reference herewith. Selecting a dosage regimen (also referred to herein as an administration regimen) for a combination therapy of the invention depends on several factors, including the serum or tissue turnover rate of the entity, the level of symptoms, the immunogenicity of the entity, and the accessibility of the target cells, tissue or organ in the individual being treated. Preferably, a dosage regimen maximizes the amount of each therapeutic agent delivered to the patient consistent with an acceptable level of side effects. Accordingly, the dose amount and dosing frequency of each therapeutic agent in the combination depends in part on the particular therapeutic agent, the severity of the cancer being treated, and patient characteristics. Guidance is selecting appropriate doses of antibodies, cytokines, and small molecules are available. See, e.g., Wawrzynczak (1996) *Antibody Therapy*, Bios Scientific Pub. Ltd. Oxfordshire, UK; Kresina (ed.) (1991) *Monoclonal Antibodies, Cytokines and Arthritis*, Marcel Dekker, New York, NY; Bach (ed.)(1193) *Monoclonal Antibodies and Peptide Therapy in Autoimmune Diseases*, Marcek Dekker, New York, NY; Beart et al, (2003) *New Engl. J. Med.* 348:601-608; Milgrom et al. (1999) *New Engl. J. Med* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348: 24-32; Lipsky et al. (2000) *New Engl. J. Med.* 343; 1594-1602; Physicians' Desk Reference 2003 (Physicians' Desk Reference, 57$^{th}$ ed); Medical Economics Company; ISBN; 1563634457; 57$^{th}$ edition (November 2002). Determination of the appropriate dosage regimen may be made by the clinician, e.g., using parameters or factors known or suspected in the art to affect treatment or predicted to affect treatment, and will depend, for example, the patient's clinical history (e.g., previous therapy), the type and stage of the cancer to be treated and biomarkers of response to one or more of the therapeutic agents in the combination therapy.

Since the virus in the combination with the checkpoint inhibitor according to the invention comprises infectious virus particles with the ability to penetrate through the blood system, treatment can be performed or at least initiated by intravenous injection of the virus. However, a preferred route of administration is intratumoral administration.

Since long-term intravenous treatment is susceptible to becoming inefficient as a result of the formation of neutralizing antibodies to the virus, different modes of administration can be adopted after an initial regimen intravenous viral administration, or such different administration techniques, e.g., intratumoral virus administration, can be alternatively used throughout the entire course of viral treatment.

As another specific administration technique, the virus (virus, vector and/or cell agent) can be administered to the patient from a source implanted in the patient. For example, a catheter, e.g., of silicone or other biocompatible material, can be connected to a small subcutaneous reservoir (Rickham reservoir) installed in the patient during tumor removal or by a separate procedure, to permit the parvovirus composition to be injected locally at various times without further surgical intervention. The virus or derived vectors can also be injected into the tumor by stereotactic surgical techniques or by navigation targeting techniques.

Administration of the virus can also be performed by continuous infusion of viral particles or fluids containing viral particles through implanted catheters at low flow rates using suitable pump systems, e.g., peristaltic infusion pumps or convection enhanced delivery (CED) pumps.

A yet another method of administration of the viral combination part is from an implanted article constructed and arranged to dispense the parvovirus to the desired cancer tissue. For example, wafers can be employed that have been impregnated with the virus, particularly parvovirus H-1, wherein the wafer is attached to the edges of the resection cavity at the conclusion of surgical tumor removal. Multiple wafers can be employed in such therapeutic intervention. Cells that actively produce the virus, or virus-based vectors, can be injected into the tumor or into the tumoral cavity after tumor removal.

It can also allow the clinical use of the virus and/or checkpoint inhibitor at lower therapeutic doses preserving or even enhancing anticancer efficacy while increasing safety and reducing and/or avoiding side effects. In view of the strong synergistic effect between the virus and checkpoint inhibitor it is possible to foresee the reduction of the therapeutic doses, e.g. half or a third of the previously used single component doses are preserving the desired therapeutic effect. In view of the reduced doses (severe) side effects may be reduced or even avoided.

In case of parvovirus the infection effects kill tumor cells but does not harm normal cells and such infection can, for example, be carried out by intratumoral use of a suitable parvovirus, e.g., parvovirus H-1, or a related virus or vectors based on such viruses, to effect tumor-specific therapy without adverse neurological or other side effects.

A combination therapy of the invention may be used prior to or following surgery to remove a tumor and may be used prior to, during or after radiation therapy.

A combination therapy of the invention is typically used to treat a tumor that is large enough to be found by palpation or by imaging techniques well known in the art, such as MRI, ultrasound, or CAT scan. In some preferred embodiments, a combination therapy of the invention is used to treat an advanced stage tumor having dimensions of at least about 200 mm$^3$, 300 mm$^3$, 400 mm$^3$, 500 mm$^3$, 750 mm$^3$, or up to 1000 mm$^3$.

The pharmaceutical combination may also comprise one or more additional therapeutic agents. The additional therapeutic agent may be, e.g., a chemotherapeutic agent, a biotherapeutic agent (including but not limited to antibodies to VEGF, EGFR, Her2/neu, VEGF receptors, other growth factor receptors, CD20, CD40, CD40L, CTLA-4, OX-40 4-1BB, and ICOS), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines (such as but not limited to GM-CSF).

Examples of chemotherapeutic agents include alkylating agents such as cyclophosphamide, busulfan, a camptothecin, chlorozotocin, fotemustine, lomustine, nimustine, ranimustine, antibiotics, bleomycins, caminomycin, dactinomycin, daunorubicin, idarubicin, 5-flourouracil (5-FU), methotrexate, cytarabine, platinum analog such as cisplatin and carboplatin; vinblastine, platinum; etoposide (VP-16); ifosfamide, mitoxantrone; vincristine; vinorelbine; novantrone; teniposide; edatrexate; daunomycin; aminopterin, xeloda; ibandronate; topoisomerase inhibitors; difluoromethylornithine (DMFO); retinoids, tamoxifen, raloxifene, droloxifene, 4-hydroxytamoxifen, trioxifene, keoxifene or aromatase inhibitors.

The present invention also relates to the use of (a) a parvovirus H-1 and (b) checkpoint inhibitor for the preparation of (a) pharmaceutical composition(s) or combination for the treatment of cancer.

The mode of administration of (a) and (b) may be simultaneously or sequentially, wherein, preferably, (a) and (b) are sequentially (or separately) administered. This means that (a) and (b) may be provided in a single unit dosage form for being taken together or as separate entities (e.g. in separate containers) to be administered simultaneously or with a certain time difference. This time difference may be between 1 hour and 1 week, preferably between 12 hours and 3 days. In addition, it is possible to administer the virus via another administration way than the checkpoint inhibitor. In this regard it may be advantageous to administer either the virus or checkpoint inhibitor intratumoraly and the other systemically or orally. In a particular preferred embodiment the virus is administered intratumoraly and the checkpoint inhibitor intravenously. Preferably, the virus and the checkpoint inhibitor are administered as separate compounds. Concomitant treatment with the two agents is also possible.

Each therapeutic agent in a combination therapy of the invention may be administered either alone or in a medicament (also referred to herein as pharmaceutical composition) which may comprise the therapeutic agent and one or more pharmaceutically acceptable carriers, excipients and diluents, according to standard pharmaceutical practice. Each therapeutic agent in a combination therapy of the invention may be administered simultaneously (i.e., in the same medicament), concurrently (i.e., in separate medicaments administered one right after the other in any order) or sequentially in any order. Sequential administration is particularly useful when the therapeutic agents in the combination therapy are in different dosage forms (one agent is a tablet or capsule and another agent is a sterile liquid) and/or are administered on different dosing schedules, e.g. a chemotherapeutic that is administered at least daily and a biotherapeutic that is administered less frequently, such as once weekly, once every two weeks, or once every three weeks.

In some embodiments, at least one of the therapeutic agents in the combination therapy is administered using the same dosage regimen (dose, frequency and duration of treatment) that is typically employed when the agent is used as monotherapy for treating the same cancer. In other embodiments, the patient receives a lower total amount of at least one of the therapeutic agents in the combination therapy than when the agent is used as monotherapy, e.g., smaller doses, less frequent doses, and/or shorter treatment duration. The checkpoint inhibitor and oncolytic virus described herein may be provided as a kit which may comprise a first container and a second container and a package insert. The first container contains at least one dose of a medicament which may comprise a checkpoint inhibitor, preferably an anti-PD-1 antagonist, the second container contains at least one dose of a medicament which may comprise an oncolytic virus, and the package insert, or label, which may comprise instructions for treating a patient for cancer using the medicaments. The first and second containers may be comprised of the same or different shape (e.g., vials, syringes and booles) and/or material (e.g. Plastic or glass). The kit may further comprise other materials that may be useful in administering the medicaments, such as diluents, filters, IV bags and lines, needles and syringes. In some preferred embodiments of the kit, the anti-PD-1 antagonist is an anti-PD-1 antibody and the instructions state that the medicaments are intended for use in treating a patient having a cancer that tests positive for PD-L1 expression by an TIC assay.

In the present invention it has been shown for the first time that the combinatorial use of an oncolytic virus, particularly parvovirus H-1PV, and a checkpoint inhibitor, particularly pembrolizumab, may be a valid approach against cancer, in particular brain tumor, colon carcinoma and pancreatic carcinomas. As outlined more detailed in the examples it was surprisingly possible to reduce metastasis size in a tumor type (CRC) which is normally not responsive to checkpoint inhibitor treatment. Even more surprisingly, a considerable tumor size reduction was obtained in an inoperable primary glioblastoma multiforme.

Without the intent of being bound to a theory, as previously mentioned tumors hide themselves from attacks by the immune system by using immune checkpoint pathways, e.g.

through binding of PD-L1 at the tumor side to the PD-1 receptor at the T-cell side. This results in immune tolerance of the body to the tumor. Immune checkpoint inhibitors are antibodies which block the immune checkpoint pathways (e.g. anti-PD-L1 or anti-PD1 antibodies). As a result the immune tolerance breaks down and the immune cells may recognize the tumor and attack it. However, this does not work for all tumor types since tumors often have a microenvironment which makes it impossible that the activated immune cells invade into the tumor. This invasion into the tumor is now made possible by using the oncolytic virus, in particular a parvovirus, more particularly parvovirus H-1, which attacks the tumor and changes its microenvironment. In other words, the oncolytic virus is able to make the tumor "naked" through oncolysis and the immune cells which have been "armed" by using the checkpoint inhibitor are able to start the invasion into the tumor. The oncolytic virus may be seen as a door opener for a successful immune response. With this concept it should be possible to treat any tumor type, also those where checkpoint inhibitor treatment failed in the past since the oncolytic virus treatment transforms a non-immunogenic tumor in an immunogenic one. In view of the general principle this works with any oncolytic virus as long as it changes the tumor microenvironment and with any checkpoint inhibitor. This could lead to long-term effects in prevention of disease relapse, potentially adding to initial oncolysis. This combination of effects renders the tumor more susceptible to the immune system, in particular after previous therapy with the virus. Patient's examples show that this combination therapy leads to either remission or stable disease.

When examining cancer progression it has been found out that an evolving crosstalk between different cells, involving especially cancer cells and immune cells, is utilized. Cancer cells can alter the immune microenvironment and the function of immune cells leading to immunosuppression and immune evasion (Fridman et al., 2012; Gabrilovich et al., 2012; Halama et al., 2011 (a), 2011 (b)). For example, in the case of liver metastases of a colorectal cancer (CRC) it has been shown that the invasive margin of colorectal cancer liver metastases is an immunological microenvironment of its own dimensions. This environment induces migration of T lymphocytes into the invasive margin following a distinct chemokine gradient. Infiltrating T lymphocytes exert tumor stimulating effects via their own production of CCL5. The microenvironment in liver metastases of colorectal cancer shows no Th1, Th2 or Th17 milieu but instead is optimized for tumor-promoting inflammation involving chemokines and growth factors like VEGF, HGF and MIF. (Halama et al., 2016). In this article a) an immunosuppressive landscape, b) a potential tumor-protective mechanism of colorectal cancer metastases and c) the tumor-promoting properties of specific immune cell subsets in tumors and metastases has been highlighted. In this publication it has also been shown that tumor cells are PD-L1 negative at the invasive margin. This may be an explanation why the treatment with checkpoint inhibitors was not so successful in several tumor entities so far. As previously mentioned, the microenvironment must be changed by the oncolytic virus before immune cells can successfully enter the tumor and attack it. In this regard reference is made to Example 2 and FIGS. 1-9 showing that after the treatment with parvovirus H-1 and PD1 antibody a significant increase in T cell density was observed in the tumor and that most T cells are PD 1 positive.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: General Methods (a) Fluorescence In Situ Hybridization (FISH)

FISH assay: The method procedure was performed essentially as described by Silahtaroglu et al (Molecular and Cellular Probes. 2003; 17:165-169) and Nehmé et al (J Neurosci Methods. 2011; 196:281-288). The FISH assay was first established in human NBK cells cultured in vitro and extended to paraffin-embedded tumor tissue deriving from human glioma xenografts in immunodefficient rats. The assay protocol was then applied for the detection of H-1PV DNA and RNA sequences in patient-derived paraffin-embedded or cryopreserved tumor material.

Positive and negative controls: In each FISH assay, paraffin-embedded tumor tissue deriving from H-1PV- or mock-treated human glioma xenografts in rats were used as positive or negative controls, respectively. No probe (reagent substitution negative control; target-specific hybridization probe omitted) and mismatch (target-specific hybridization probe with 3-5 nucleotides swapped) controls were also included.

Hybridization probes: The target-specific hybridization probes were custom-designed by Exiqon (Vedbaek, Denmark) to recognize H-1PV non-structural (NS) and structural (VP) protein coding sequences and represented locked nucleic acid (LNA) oligonucleotides with increased target specificity and high-potency binding (for a reference, see www.exiqon.com). The probes were synthetized by reverse complementation either to H-1PV negative (sense) or positive (antisense) strand DNA and were double digoxin (DIGN)-labeled at their 3' and 5' ends. Both NS- and VP-specific probes were applied as a mix of equal amounts, in order to increase the hybridization signal.

NS1-antisense:
5DIGN/TCAGCACACAACAGATGGCAT/3DIGN
(SEQ ID NO: 1)
VP-antisense:
5DIGN/TACTATCCAGAGCAACCATCAT/3DIGN
(SEQ ID NO: 2)
NS1-sense:
5DIGN/AATTCGCTAGGTTCAATGCGCT/3DIGN
(SEQ ID NO: 3)
VP-sense:
5DIGN/TGACCTACCAACATCAGATACA/3DIGN
(SEQ ID NO: 4)

Signal visualization: Signal visualization was achieved by sequential incubation with anti-DIGN antibody conjugated with horseradish peroxidase (Roche, Sigma-Aldrich, Munich, Germany), and the Tyramide Signal Amplification (TSA)/cyanine (Cy) 3 reagent (Perkin Elmer, Germany). Image acquisition was performed by using a Zeiss Cell Observer microscope and the ZEN software.

Signal quantitation: For the quantitative analysis of positive signals the Fiji ImageJ software was used, and an automated analysis using purpose-developed custom macros (Dr. D. Krunic, German Cancer Research Center, Heidelberg, Germany) and constant processing settings was conducted. Results were presented as average intensity of positive signals per microscope observation field (dFOV=1.000 µm) and/or as average intensity of positive signals per labeled cell. The value of the background fluorescence (false-positive signals generated by the mismatched probe) defined the cut-off between positive and negative signals. Signal intensity was expressed in arbitrary units (a.u.).

(b) Cell Culture & Proliferation Assays

T cells were drawn from healthy donors and after a short period of rest were stimulated in CD3/CD28 coated 96 well plates (anti-CD3 from BioLegend, USA, anti-CD8 from BD, Germany) overnight. T cell culture media contained RPMI 1640 (PAA, USA), 10% human serum (heat-inactivated for 30 minutes at 56° C.), 1% Glutamine (PAA, USA), 1% penicillin/streptomycine (PAA, USA), 1% Non-essential amino acids (PAA, USA) and 1% HEPES (PAA, USA). Commercial tumor cell lines were cultured according to the suppliers instructions. Quantification of cells was performed in triplicates with double measurements with the automated cell counter TC10 (BioRad, Germany), especially directly after seeding (i.e. $0.5*10^5$ cells/ml for proliferation assays, cells equally seeded in plates) and after incubation/treatment. Primary cell lines were authenticated using Multiplex Cell Authentication by Multiplexion (Heidelberg, Germany) as described recently (Castro et al., 2013). The SNP profiles matched known profiles were unique, consistent with a human epithelial tumor cell line. All cell lines were tested for *Mycoplasma* contamination by PCR.

Preparation of ascites (from colorectal cancer patients) and extraction of macrophages and lymphocytes was performed as follows. Adapted from previous reports ascites was collected into sterile plastic bags. The outlet nozzle of each bag was prepared by disinfection with 70% alcohol and the first fraction of ascites is discarded while the remaining ascites is distributed in 50 ml Falcon tubes. Centrifugation with 1500 rpm for 10 min. Supernatants were mixed with RPMI medium (1:2) and used as conditioned medium (CM). For macrophage populations (a), pellets were then resuspended in RPMI medium and are run through a Ficoll gradient (30 min at 2000 rpm at room temperature). The interphase was then collected in RPMI, washed and centrifuged (1800 rpm for 10 min) and the resulting pellets are then seeded into cell flasks with RPMI. For macrophage populations the supernatants were then harvested after an adherence step of 1.5 h (37° C.), the remaining adherent cells were washed with PBS (three times) and then supplemented with CM. For lymphocytes (b), pellets were then resuspended in RPMI medium centrifuged again and pellets were then seeded into cell flasks with RPMI. After adherence, the supernatant was used to extract lymphocytes. After experiments with either the macrophages or lymphocytes the supernatant was measured for cytokines and the cells were harvested and analyzed with stainings (double staining CD163 and CD68 for macrophages, CEA for tumor cells and CD3 for lymphocytes) and controlled for purity of cell content (>95%). Extraction of tumor cells was performed after dissociation of tumor tissue and adhesion steps.

(c) Cytokine & Chemokine Quantification

A two-laser array reader simultaneously quantifies all cytokines and chemokines of interest. Standard curves and concentrations were calculated with Bio-Plex Manager 4.1.1 on the basis of the 5-parameter logistic plot regression formula. Briefly, small pieces of dissected frozen tissue were transferred in 150 µl cold lysis buffer, vortexed, frozen at −80° C. (10 min) and thawed on ice. After incubation in a cold ultrasonic bath (10 min), samples were frozen again at −80° C., thawed on ice and centrifuged (13.000 rpm, 20 min, 4° C.). The protein concentration of the supernatant was determined and the concentration of lysates was adjusted to 1000 µg/ml (300 µg/ml for biopsies) using human serum diluent (BioRad) and cytokine/chemokine concentrations in tissue lysates were quantified by multiplex protein arrays, according to manufacturer's instructions (BioRad Laboratories, Hercules, CA, USA). The detection sensitivity of the analytes ranged from 1 µg/ml to 100 ng/ml. Values that were identified as "Out of range" by the platform were extrapolated based on the single standard curves that were generated for each analyte. As standard curves showed minimal standard deviations the highest concentrated standard concentration was used for the extrapolation. To form classes of cytokines (in descending order e.g. TH1, TH2, TH17 etc.) the AMIGO database was used (amigo.geneontology.org/) in evaluating specific terms (e.g. GO:0043030: regulation of macrophage activation, GO:0042104: positive regulation of activated T cell proliferation or GO:0006935: chemotaxis) or literature search. Positive controls from samples with TH1, TH2 or TH17 dominated cytokines were used for analysis.

General reproducibility (precision) of the multiplex protein quantification approach on serial sections showed an excellent reproducibility (Spearman's Rank correlation with r=0.975 and p=0.0001, median difference 70 pg/ml). Accuracy was evaluated in measurements of solutions with known concentrations of the cytokine, e.g. CCL5 at 25.000 pg/ml which showed a standard deviation of 628.92 pg/ml, corresponding to 2.5% from the expected value and CCL5 at 100 pg/ml which showed a standard deviation of 2.7 pg/ml, corresponding to 2.7% from the expected value. Calibration of the investigated analytes is performed as recommended by the manufacturer (BioRad, Germany) and we refer to the manufacturer's homepage for additional reference material on accuracy and precision (www.bio-rad.com/webroot/web/pdf/lsr/literature/Bulletin5803A.pdf).

Comparison between different serial section invasive margin protein quantifications also revealed an excellent reproducibility (spearman's rank correlation rho=0.922, p=0.0001). Finally the comparison of the ratios of laser-assisted microdissected material to macrodissected material revealed that the invasive margin indeed is a precisely separated region with reproducible and distinct cytokine profiles. Also, the differences to the surrounding adjacent liver or the liver metastasis are so pronounced that the macrodissected specimen completely resembles the patterns found in the microdissected specimen.

Generation of cytokine and chemokine data from biopsy material was performed as outlined above. Due to the limitations in the amount of material available, the protein concentrations used for the assays was set to 300 mg. Histologically the adjacent liver of the patients remained unchanged under treatment as compared to before treatment, with respect to morphology and immune cell presence. Therefore, as control for the precision of the cytokine measurement (and to assess effects of dilution etc.) the cytokine levels of the adjacent liver before and under treatment were used and showed excellent concordance (spearman's rank correlation rho=0.991 and p=0.0001, median difference 5 µg/ml). This also makes effects of wound healing (that should not be present anymore after day 8 post-biopsy) unlikely to interfere with the effects of CCR5 inhibition. The percentage of apoptotic tumor cells was determined by counting apoptotic nuclei (based on nuclear morphology) and intact tumor cells in sections stained with hemalaun and/or H&E as described previously (Duan et al., 2003).

(d) Immunohistochemistry & Immunofluorescence

FFPE tissues were deparaffinized and rehydrated (BOND Dewax Solution, Leica, Germany). After heat-induced epitope retrieval (HIER) at 100° C. (BOND Epitope Retrieval Solution 1 or 2, Leica, Germany), endogenous peroxidase activity was blocked by incubation with 3% peroxide block for 20 min (BOND Polymer Refine Detection System, Leica, Germany). The sections were blocked with 10% normal goat serum (Vector, USA). A list of the used antibodies and dilutions can be found below. These were applied as primary antibodies at room temperature for 30 min. The slides were incubated with a secondary antibody (rabbit-anti-mouse IgG, Bond Polymer Refine Detection System, Leica, Germany) for 8 min at room temperature. Further amplification of the signal was achieved through incubation with a third antibody, conjugated with horse radish peroxidase and coupled to dextrane molecules in large numbers, for 8 min at room temperature (Poly-HRP-mouse-anti-rabbit IgG, Bond Polymer Refine Detection System, Leica, Germany). The antigen detection was performed by a color reaction with 3,3-di-amino-benzidine (DAB chromogen, Bond Polymer Refine Detection System, Leica, Germany). The sections were counterstained with hematoxylin (Bond Polymer Refine Detection System, Leica, Germany) and mounted with Aquatex (Merck, Germany). Matched isotype controls were used a negative control and adjacent normal tissue or known positive cells were used as positive control.

Immunofluorescence double staining was performed on cryosections using a red fluorescence Alexa Fluor 594 dye-labeled donkey-anti-mouse IgG (Life Technologies, Germany) and a green fluorescence Alexa 488 dye-labeled goat-anti-rabbit IgG (Life Technologies, Germany) sequentially for the chemokine double stainings (or in case of green fluorescence Alexa 488 dye-labeled goat-anti-mouse IgG the second primary antibody was omitted for control). For the analysis of CD68, PD-L1, CD4, CD8 and CCL5 a red fluorescence Alexa Fluor 594 dye-labeled donkey anti-rabbit IgG (Invitrogen, Germany) and a green fluorescence Alexa 488 dye-labeled goat-anti-mouse IgG (Life Technologies, Germany) were used simultaneously. For the analysis of CD3 and CCL5 Alexa Fluor555 goat anti-mouse IgG (H+L) molecular probes A21422 and Alexa Fluor 488 goat anti-rabbit IgG were used. Cryo sections were fixed either with 4% PFA or 33% acetone in methanol prior to staining according to antibody recommendations. After incubation of the first primary antibody overnight at 4° C., Alexa Fluor 594 (1:100 dilution) was applied for 1 hour. The second primary antibody was applied for 3 hours at room temperature and detected with Alexa Fluor 488 (1:100 dilution) for 1 hour during sequential double staining. For simultaneous staining both primary antibodies were incubated overnight following both Alexa Fluor antibodies (1:100 dilution each) for 1 hour. Sections were mounted using Vectashield with DAPI (Vector, USA) for counterstain. Confocal images were obtained on a Nikon C2 Plus confocal microscope system.

Mouse monoclonal antibodies recognizing human CD3epsilon (1:100 dilution and HIER1 for FFPE, 4% PFA fixation and HIER2 for cryo sections, clone PSi, Novocastra, UK and rabbit monoclonal anti-CD3, clone Sp7 from Abcam), CD8 (1:50 dilution and HIER2 for FFPE, 1:100 dilution and 4% PFA fixation and for cryo sections, clone 4B11, Novocastra, UK), CCR5 (1:50 dilution and HIER1 for FFPE, 1:100 dilution, 4% PFA fixation and HIER1 for cryo sections, clone MM0065-6H20, abcam, UK), CCL5 (1:50 dilution and 4% PFA fixation for cryo sections, clone VL1, BioLegend, USA), PD1 (1:50 dilution and HIER1 for FFPE, 33% acetone in methanol fixation for cryo sections, clone NAT, abcam, UK), CD68 (1:200 dilution and HIER1 for FFPE, 1:700 dilution and 33% acetone in methanol fixation for cryo sections, clone KP1, abcam, UK), CD163 (1:500 dilution and HIER2 for FFPE, 33% acetone in methanol fixation for cryo sections, clone EDHu-1, AbD Serotec, UK), CD44 (1:9000 dilution and HIER1 for FFPE, 1:5000 dilution, 4% PFA fixation and HIER2 for cryo sections, clone 156-3C11, abcam, UK), CD74 (1:50 dilution and HIER 1 for FFPE, 1:75 dilution, 4% PFA fixation and HIER2 for cryo sections, clone LN2, abcam, UK), Ki67 (1:200 dilution, PFA fixation, clone MIB-1, DAKO, USA). CCR1 (1:50 dilution and HIER1 for FFPE, 4% PFA fixation and HIER1 for cryo sections, clone MM0061-7B17, abcam, USA), CXCL9 (1:100 dilution and 33% acetone in methanol fixation for cryo sections, clone MM0220-7F11, abcam, UK), CD11b (1:50 dilution and 33% acetone in methanol fixation for cryo sections, clone 2Q902, abcam, UK) and CXCL10 (1:50 dilution and 33% acetone in methanol fixation for cryo sections, clone 6D4, abcam, UK), interferon-alpha2 (1:50 dilution, clone EBI-1, eBioscience) and interferon-gamma (1:00 dilution, clone B27, BioLegend). Rabbit antibodies recognizing human PD-L1 (1:50 dilution and HIER2 for FFPE, 1:150 dilution and 4% PFA fixation for cryo sections, polyclonal, abcam, UK), CCR3 (1:800 dilution, HIER1 and 4% PFA fixation for cryo sections, clone Y31, abcam, UK), CD4 (1:150 dilution and 4% PFA fixation for cryo sections, clone SP35, Zytomed Systems, Germany), CD11b (1:500 dilution and 4% PFA fixation, clone EP1345Y, abcam, UK), CD8 (1:150 dilution and 4% PFA fixation for cryo sections, clone SP16, Zytomed Systems, Germany) and CEACAM5 (1:100 dilution, clone 327, Sino Biological). Classical H&E and TUNEL staining was performed according to manufacturer's description (In situ cell death detection kit, Roche, Germany) and serial sections were used to quantify dead tumor cells by comparing TUNEL vs. morphological analysis. As the side-by-side comparison of tissue sections confirmed the excellent diagnostic value of morphological analysis as published previously (Duan et al., 2003), morphological analysis was the preferred method for evaluation.

(e) Whole Slide (Immune) Cell Quantification

The number of stained immune cells was counted using a computerized image analysis system consisting of a NDP Nanozoomer (Hamamatsu Photonics, Japan) attached to a personal computer. Complete microscopic images of full tissue sections were automatically obtained (virtual microscopy) and the average cell density across the measured region was used for analysis. Cell counts were generated with a specifically developed software program (VIS software suite, Visiopharm, Denmark) across a given region of interest (on average 10 mm$^2$, with up to 40 mm$^2$) as reported previously (Halama et al., 2011b; Halama et al., 2010; Halama et al., 2009b). All evaluations were visually checked for consistency.

(f) Flow Cytometry

For each experiment, tissue from the invasive margin of colorectal cancer liver metastases (up to 10 g) was dissociated by cutting and multiple washing steps using a 40 μm cell strainer and RPMI medium. The extracted cells were then placed in a 24-well plate with RPMI medium (supplemented by 10% FCS) overnight and then optionally blocked with Monensin (BD Biosciences, Germany) for three hours.

Cells were then harvested, centrifuged and analyzed for CD3, CD8, CD4 and CCL5 using flow cytometry standard protocols.

Surface staining was performed as follows: for each 100 μl FACS buffer 2.5 μl CD3-V450 (560365, BD, Germany), 1.25 μl CD4-PerCP-Cy5.5 (560650, BD, Germany) and 2.5 μl CD8-APC-H7 (641400, BD Biosciences, Germany) were used, followed by 20 min incubation on ice (protected from light) and centrifugation. Intracellular staining was then performed by taking up cells into 1% PFA and incubation for 15 min followed by three washing steps with 0.1% Saponin buffer (and centrifugation). Staining of CCL5 was performed as follows: for each 100 μl 0.1% Saponin buffer 5 μl anti-human-RANTES (CCL5)-eFluor660 (AF647, eBioscience, UK) or isotype control mouse IgG2bk-eFluor660 with 1.25 μl (AF647, eBioscience, UK) were used, followed by 15 min incubation at room temperature (protected from light) and two washing steps with 0.1% Saponin buffer. Labeled cells were then subjected to FACS using a BD Biosciences FACS Canto II cytometer (Harvard Stem Cell Institute), gated against negative controls.

To establish the positive control prior to measuring the tumor tissue and to identify lymphocyte populations, healthy donor lymphocytes were treated as outlined above.

Example 2: Combined Modality Treatment with Parvovirus H-1 and Checkpoint Inhibitor in a Patient Having a Metastasizing CRC (Colorectal Cancer)

A patient suffering from colorectal cancer (poorly differentiated adenocarcinoma of colon transversum; mutation status: KRAS WT, NRAS WT, MSS; first surgery 2013) with progressing liver metastases (progression in size and number) was treated with a cumulative dose of $1.2 \times 10^9$ PFU parvovirus H-1 applied in three consecutive daily infusions ($4 \times 10^8$ pfu; day 1-3), followed by treatment with the immune checkpoint inhibitor pembrolizumab (Keytruda®) according to the manufacturer's posology (2 mg/Kg/BW, day 1). This treatment with the same dosage regimen was repeated after 5 weeks.

Biopsies performed on the liver metastasis were taken prior to treatment and at various time points during the treatment with the following surprising findings: in comparison to the first biopsy which was prior to the H-1PV+ pembrolizumab treatment, lymphocytic infiltration was observed which increased in later biopsies (second and third biopsies). Furthermore, imaging analysis (ultrasound, CT, MRI) revealed a mass reduction of the liver metastases.

Reference is made to FIG. 1-9 which show that during the treatment a significant increase in T cell density, with a dominant CD8+ T cell population, was observed. The T cell infiltrates are heterogenous with striking vicinity of T cells with tumor cells. Most T cells are PD1 positive.

Cytokine and chemokine quantification has been performed using the method as described in Example 1 above. The profiles are shown in FIG. 10 to 15. Increases of IP10 and CCL5 seem to be prevailing. There was no increase in IL-2 and only mild increases in interferon gamma.

A FISH analysis was performed as described in Example 1 (a) above. It shows that active virus (H-1 PV) can be determined in the biopsy 2. This is a clear indication that the virus migrated into the tumor/metastases.

Example 3: Combined Modality Treatment with Parvovirus H-1 and Checkpoint Inhibitor in a Primary Inoperable GBM (Glioblastoma Multiforme) Patient A patient suffering from inoperable glioblastoma multiforme was treated with a cumulative dose of $1.2 \times 10^9$ PFU parvovirus H-1 applied in three consecutive daily infusions, followed by treatment with pembrolizumab (Keytruda®) according to the manufacturer's posology (2 mg/Kg/BW, 3 days after H1-PV administration).

Figure 16:
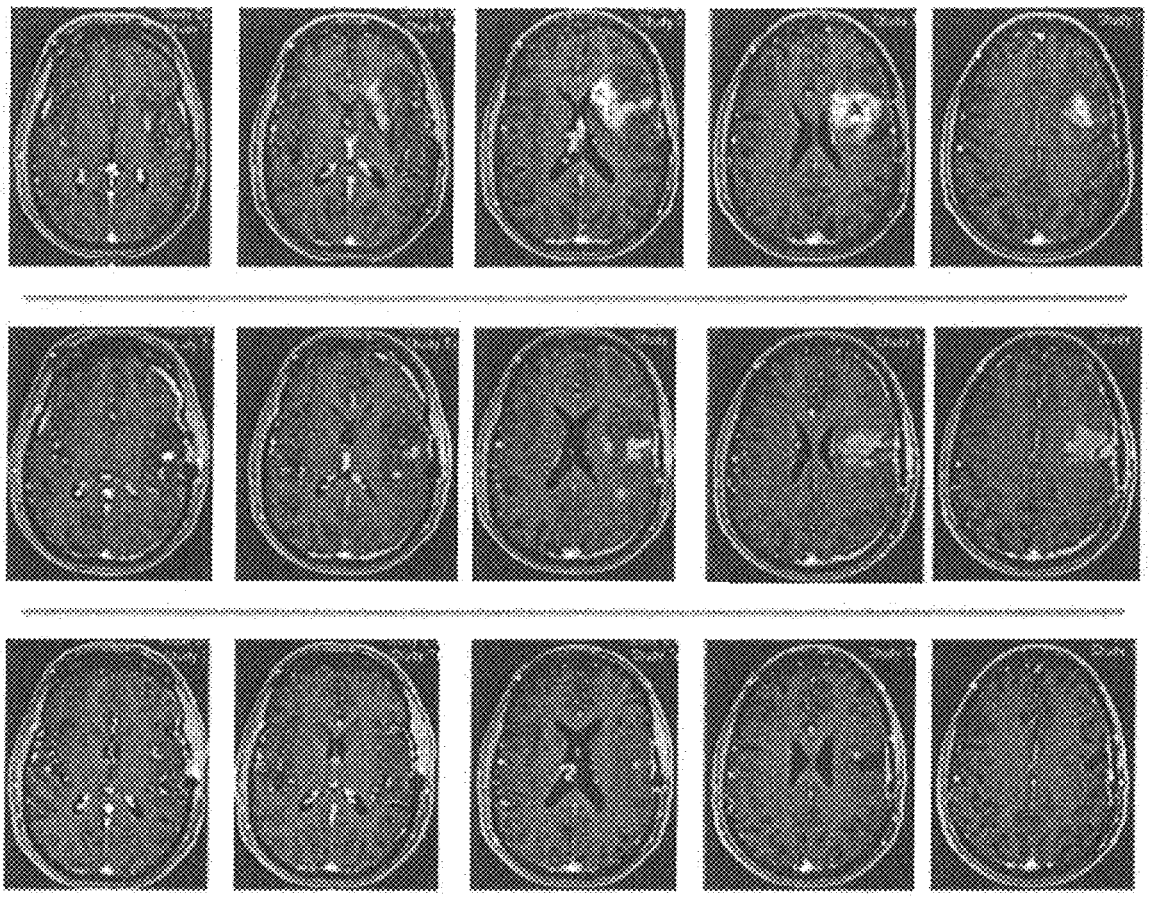
FIG. 16: MRI of progressing recurrent glioblastoma multeforme prior to treatment and during treatment (55 and 101 days after administration of H-1 PV+pembrolizumab)
Upper row: Prior to treatment with H-1 PV+Pembrolizumab
Middle row: 55 days after administration of H-1 PV+Pembrolizumab
Lower row: 101 days after administration of H-1 PV+Pembrolizumab.

MRI was taken prior to the therapy and during the treatment with the H-1 PV+checkpoint inhibitor pembrolizumab. It revealed a size reduction of the tumor exceeding 30% after 55 days of treatment and a nearly complete remission at day 101. The patient is doing well and does not require any additional medication. The MRIs are shown in FIG. 16.

LIST OF REFERENCES

Breitbach C J, Burke J, Jonker D, Stephenson J, Haas A R, Chow L Q, Nieva J, Hwang T H, Moon A, Patt R et al (2011) Intravenous delivery of a multi-mechanistic cancer-targeted oncolytic poxvirus in humans. Nature 477: 99-102.

Castro, F., Dirks, W. G., Fahnrich, S., Hotz-Wagenblatt, A., Pawlita, M., and Schmitt, M. (2013). High-throughput SNP-based authentication of human cell lines. Int J Cancer 132, 308-314.

Cotmore S F, Tattersall P (2007) Parvoviral host range and cell entry mechanisms. Adv Virus Res 70: 183-232.

Di Piazza M, Mader C, Geletneky K, Herrero y Calle M, Weber E, Schlehofer J, Deleu L, Rommelaere J (2007) Cytosolic Activation of Cathepsins Mediates Parvovirus H-1-Induced Killing of Cisplatin and TRAIL-Resistant Glioma Cells. Journal of Virology 81: 4186-4198.

Duan et al., 2003; J. Pathol. 199, 221-228.

Geletneky K, Huesing J, Rommelaere J, Schlehofer J R, Leuchs B, Dahm M, Krebs O, von Knebel Doeberitz M, Huber B, Hajda J (2012) Phase I/IIa study of intratumoral/intracerebral or intravenous/intracerebral administration of Parvovirus H-1 (ParvOryx) in patients with progressive primary or recurrent glioblastoma multiforme: ParvOryx01 protocol. BMC cancer 12: 99.

Fridman, W. H., Pages, F., Sautes-Fridman, C., and Galon, J. (2012). The immune contexture in human tumours: impact on clinical outcome. Nat Rev Cancer 12, 298-306.

Gabrilovich, D. I., Ostrand-Rosenberg, S., and Bronte, V. (2012). Coordinated regulation of myeloid cells by tumours. Nat Rev Immunol 12, 253-268.

Halama, N., Braun, M., Kahlert, C., Spille, A., Quack, C., Rahbari, N., Koch, M., Weitz, J., Kloor, M., Zoernig, I., et al. (201 1a). Natural Killer Cells are Scarce in Colorectal Carcinoma Tissue Despite High Levels of Chemokines and Cytokines. Clinical cancer research: an official journal of the American Association for Cancer Research 17, 678-689.

Halama, N., Michel, S., Kloor, M., Zoernig, I., Benner, A., Spille, A., Pommerencke, T., von, K.n.e.b.e.l. D. M., Folprecht, G., Luber, B., et al. (2011b). Localization and Density of Immune Cells in the Invasive Margin of Human Colorectal Cancer Liver Metastases Are Prognostic for Response to Chemotherapy. Cancer Res 71, 5670-5677.

Halama, N., Michel, S., Kloor, M., Zoernig, I., Pommerencke, T., von Knebel Doeberitz, M., Schirmacher, P., Weitz, J., Grabe, N., and Jager, D. (2009a). The localization and density of immune cells in primary tumors of human metastatic colorectal cancer shows an association with response to chemotherapy. Cancer immunity 9, 1.

Halama, N., Spille, A., Lerchl, T., Brand, K., Herpel, E., Welte, S., Keim, S., Lahrmann, B., Klupp, F., Kahlert, C., et al. (2013). Hepatic metastases of colorectal cancer are rather homogeneous but differ from primary lesions in terms of immune cell infiltration. Oncoimmunology 2, e24116.

Halama, N., Zoernig, I., Spille, A., Michel, S., Kloor, M., Grauling-Halama, S., Westphal, K., Schirmacher, P., Jaeger, D., and Grabe, N. (2010). Quantification of prognostic immune cell markers in colorectal cancer using whole slide imaging tumor maps. Anal Quant Cytol Histol 32, 333-340.

Halama, N., Zoernig, I., Spille, A., Westphal, K., Schirmacher, P., Jaeger, D., and Grabe, N. (2009b). Estimation of Immune Cell Densities in Immune Cell Conglomerates: An Approach for High-Throughput Quantification. PLoS One 4, e7847.

Halama et al. (2016), "Tumoral immune cell exploitation in colorectal cancer liver metastases can be targeted effectively by anti-CCR5 therapy in cancer patients"; Cancer Cell, in press.

Hristov G, Kramer M, Li J, El-Andaloussi N, Mora R, Daeffler L, Zentgraf H, Rommelaere J, Marchini A (2010) Through Its Nonstructural Protein NS1, Parvovirus H-1 Induces Apoptosis via Accumulation of Reactive Oxygen Species. J Virol 84: 5909-5922.

Nuesch J P, Lacroix J, Marchini A, Rommelaere J (2012) Molecular pathways: rodent parvoviruses-mechanisms of oncolysis and prospects for clinical cancer treatment. Clin Cancer Res 18: 3516-3523.

Ohshima T, Iwama M, Ueno Y, Sugiyama F, Nakajima T, Fukamizu A, Yagami K (1998) Induction of apoptosis in vitro and in vivo by H-1 parvovirus infection. The Journal of general virology 79 (Pt 12): 3067-3071.

Ran Z, Rayet B, Rommelaere J, Faisst S (1999) Parvovirus H-1-induced cell death: influence of intracellular NAD consumption on the regulation of necrosis and apoptosis. Virus Res 65: 161-174.

Rayet B, Lopez-Guerrero J A, Rommelaere J, Dinsart C (1998) Induction of programmed cell death by parvovirus H-1 in U937 cells: connection with the tumor necrosis factor alpha signalling pathway. J Virol 72: 8893-8903.

Russell S J, Peng K W, Bell J C (2012) Oncolytic virotherapy. Nat Biotechnol 30: 658-670.

Ueno Y, Harada T, Iseki H, Ohshima T, Sugiyama F, Yagami K (2001) Propagation of rat parvovirus in thymic lymphoma cell line C58(NT)d and subsequent appearance of a resistant cell clone after lytic infection. J Virol 75: 3965-3970.

The invention is further described by the following numbered paragraphs:

1. A pharmaceutical combinationcontaining (a) parvovirus H-1 and (b) an anti-PD1 antibody or an anti-PD-L1 antibody.
2. The pharmaceutical combination of paragraph 1, wherein the anti-PD1-antibody is pembrolizumab or nivolumab.
3. The pharmaceutical combination of paragraph 1 or 2, further comprising one or more additional therapeutic agents selected from chemotherapeutic agents, biotherapeutic agents, an immunogenic agents, immune stimulating cytokines and cells transfected with genes encoding immune stimulating cytokines.
4. The pharmaceutical combination as defined in any of paragraphs 1-3 for use in a method of treating cancer.
5. The pharmaceutical combination for the use according to paragraph 4, wherein (a) parvovirus H-1 and (b) the anti-PD1 antibody or the anti-PD-L1 antibody are sequentially administered.
6. The pharmaceutical combination for the use according to paragraph 4 or 5, wherein the use is for treating solid tumors, haematological cancer and/or cancer initiating stem cells.
7. The pharmaceutical combination for the use according to any of paragraphs 4 to 6, wherein the cancer is brain cancer, colon cancer, bladder cancer, liver cancer, breast cancer, kidney cancer, head/neck squamous cell carcinoma, lung cancer, malignant melanoma, ovarian cancer, pancreatic cancer, prostate cancer, renal cell cancer or stomach cancer.
8. The pharmaceutical combination for the use according to any of paragraph 7, wherein the brain cancer is glioblastoma multiforme.
9. The pharmaceutical combination for the use according to any one of paragraphs 4 to 8, wherein (a) parvovirus H-1 and/or (b) the anti-PD1 antibody or the anti-PD-L1 antibody are administered by intratumoral or intravenous administration.
10. A kit which comprises a first container, a second container and a package insert, wherein the first container comprises at least one dose of a pharmaceutical composition containing parvovirus H-1, the second container comprises at least one dose of a pharmaceutical composition comprising an anti-PD1 antibody or an anti-PD-L1 antibody, and the package insert comprises instructions for treating an individual having cancer using the pharmaceutical composition(s).
11. The kit of paragraph 10, wherein the cancer is brain cancer, colon cancer, bladder cancer, liver cancer, breast cancer kidney cancer, head/neck squamous cell carcinoma, lung cancer, malignant melanoma, ovarian cancer, pancreatic cancer, prostate cancer, renal cell cancer or stomach cancer.
12. The kit of paragraph 11, wherein the brain cancer is glioblastoma multiforme.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of treating cancer comprising administering a pharmaceutical combination containing (a) parvovirus H-1 and (b) an anti-PD1 antibody or an anti-PD-L1 antibody.

2. The method according to claim 1, wherein (a) parvovirus H-1 and (b) the anti-PD1 antibody or the anti-PD-L1 antibody are sequentially administered.

3. The method according to claim 1, wherein the method comprises treating solid tumors, haematological cancer and/or cancer initiating stem cells.

4. The method according to claim 1, wherein the cancer is brain cancer, colon cancer, bladder cancer, liver cancer, breast cancer, kidney cancer, head/neck squamous cell carcinoma, lung cancer, malignant melanoma, ovarian cancer, pancreatic cancer, prostate cancer, renal cell cancer or stomach cancer.

5. The method according to claim 4, wherein the brain cancer is glioblastoma multiforme.

6. The method according to claim 1, wherein (a) parvovirus H-1 and/or (b) the anti-PD1 antibody or the anti-PD-L1 antibody are administered by intratumoral or intravenous administration.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: artificial sequence
<220> FEATURE:
<223> OTHER INFORMATION: probe NS1 antisense

<400> SEQUENCE: 1

```
tcagcacaca acagatggca t                                              21

<210> SEQ ID NO 2
<211> LENGTH: 22
<212> TYPE: DNA
<213> ORGANISM: artificial sequence
<220> FEATURE:
<223> OTHER INFORMATION: VP antisense

<400> SEQUENCE: 2
tactatccag agcaaccatc at                                             22

<210> SEQ ID NO 3
<211> LENGTH: 22
<212> TYPE: DNA
<213> ORGANISM: artificial sequence
<220> FEATURE:
<223> OTHER INFORMATION: probe NS-1 sense

<400> SEQUENCE: 3
aattcgctag gttcaatgcg ct                                             22

<210> SEQ ID NO 4
<211> LENGTH: 22
<212> TYPE: DNA
<213> ORGANISM: artificial sequence
<220> FEATURE:
<223> OTHER INFORMATION: VP sense

<400> SEQUENCE: 4
tgacctacca acatcagata ca                                             22
```